US009072463B2

(12) United States Patent
Sanders et al.

(10) Patent No.: US 9,072,463 B2
(45) Date of Patent: Jul. 7, 2015

(54) PROSTHETIC LIMB MONITORING SYSTEM

(75) Inventors: Joan Sanders, Sammamish, WA (US);
Timothy Myers, Seattle, WA (US);
Brian Hafner, Seattle, WA (US)

(73) Assignee: University of Washington, Seattle, WA (US)

( * ) Notice: Subject to any disclaimer, the term of this patent is extended or adjusted under 35 U.S.C. 154(b) by 846 days.

(21) Appl. No.: 12/694,409

(22) Filed: Jan. 27, 2010

(65) Prior Publication Data

US 2010/0191153 A1    Jul. 29, 2010

Related U.S. Application Data

(60) Provisional application No. 61/147,663, filed on Jan. 27, 2009.

(51) Int. Cl.
*A61B 5/103*    (2006.01)
*A61B 5/11*    (2006.01)
*A61B 5/00*    (2006.01)

(52) U.S. Cl.
CPC ............. *A61B 5/1038* (2013.01); *A61B 5/4585* (2013.01); *A61B 5/112* (2013.01)

(58) Field of Classification Search
CPC ........ A61B 5/11; A61B 5/112; A61B 5/1038; A61B 5/4528; A61B 5/4585; A61B 2562/0219; A61B 2019/464; A61B 2019/465; A61B 2019/466
USPC .......................................... 600/587, 592, 595
See application file for complete search history.

(56) References Cited

U.S. PATENT DOCUMENTS

| 4,195,643 | A | 4/1980 | Pratt, Jr. |
| 5,280,429 | A | 1/1994 | Withers ................... 364/413.15 |
| 5,771,310 | A | 6/1998 | Vannah |
| 5,827,209 | A | 10/1998 | Gross |
| 5,993,400 | A | 11/1999 | Rincoe et al. |

(Continued)

FOREIGN PATENT DOCUMENTS

WO    WO 2010/088262 A2    8/2010

OTHER PUBLICATIONS

Armstrong et al., "Bioimpedance spectroscopy technique: Intra-, extracellular, and total body water." *Medicine & Science in Sports & Exercise* vol. 29(12): 1657-1663, 1997.

(Continued)

*Primary Examiner* — Adam Eiseman
(74) *Attorney, Agent, or Firm* — Kilpatrick Townsend and Stockton LLP

(57) ABSTRACT

Parameters related to use of a prosthesis by a patient with a limb amputation are monitored using a tool that includes one or more piezoelectric force sensors. The resulting data are processed for use both in short and long term management of amputee patients. The sensor is a small modular unit that fits within or between traditional prosthetic components, e.g., below a prosthesis socket. The data produced by the tool are collected, processed, and stored. Optionally, the data are periodically communicated to a remote site via a network, e.g., over the Internet. The device and associated software used to process the data can be used to characterize activities conducted by a prosthesis user, to determine pistoning or threatening interface stress distributions between the limb and socket, mal-alignment of the socket, use of improper components, and other possibly undesired conditions that the amputee patient using the prosthesis may be experiencing.

33 Claims, 12 Drawing Sheets

(56) References Cited

U.S. PATENT DOCUMENTS

| | | | |
|---|---|---|---|
| 6,125,297 A | 9/2000 | Siconolfi | 600/547 |
| 6,151,523 A | 11/2000 | Rosell Ferrer et al. | 600/547 |
| 6,610,101 B2 | 8/2003 | Herr et al. | |
| 6,666,831 B1 | 12/2003 | Edgerton et al. | |
| 6,690,181 B1 | 2/2004 | Dowdeswell et al. | 324/691 |
| 6,927,858 B2 | 8/2005 | Boone et al. | 356/437 |
| 7,150,762 B2 | 12/2006 | Caspers | 623/27 |
| 7,179,234 B2* | 2/2007 | Nashner | 600/595 |
| 7,217,247 B2 | 5/2007 | Dariush et al. | |
| 7,251,593 B2 | 7/2007 | Dariush et al. | |
| 7,279,009 B2 | 10/2007 | Herr et al. | |
| 7,310,999 B2 | 12/2007 | Miller | 73/149 |
| 7,507,259 B2 | 3/2009 | Townsend et al. | |
| 7,713,217 B2 | 5/2010 | Ikeuchi et al. | |
| 7,794,505 B2 | 9/2010 | Clausen et al. | |
| 7,799,091 B2 | 9/2010 | Herr et al. | |
| 7,850,740 B2 | 12/2010 | Cox et al. | |
| 7,862,620 B2 | 1/2011 | Clausen et al. | |
| 7,867,285 B2 | 1/2011 | Clausen et al. | |
| 7,981,059 B2 | 7/2011 | Ueda et al. | |
| 8,116,900 B2 | 2/2012 | Slemker et al. | |
| 8,324,975 B2 | 12/2012 | Stein | |
| 8,452,458 B2 | 5/2013 | Even-Zohar | |
| 2001/0029343 A1 | 10/2001 | Seto et al. | |
| 2002/0052663 A1 | 5/2002 | Herr et al. | |
| 2003/0120183 A1 | 6/2003 | Simmons | |
| 2004/0039454 A1 | 2/2004 | Herr et al. | |
| 2004/0116836 A1 | 6/2004 | Kawai et al. | |
| 2004/0158175 A1 | 8/2004 | Ikeuchi et al. | |
| 2004/0167638 A1 | 8/2004 | Caspers | |
| 2004/0249319 A1 | 12/2004 | Dariush | |
| 2005/0113932 A1 | 5/2005 | Kovacevic | |
| 2005/0165284 A1 | 7/2005 | Gefen | |
| 2006/0020348 A1 | 1/2006 | Slemker et al. | |
| 2006/0095135 A1 | 5/2006 | Kovacevic | |
| 2006/0195197 A1 | 8/2006 | Clausen et al. | |
| 2006/0206214 A1 | 9/2006 | Clausen et al. | |
| 2006/0206215 A1 | 9/2006 | Clausen et al. | |
| 2007/0021689 A1* | 1/2007 | Stergiou et al. | 600/595 |
| 2007/0027402 A1 | 2/2007 | Levin et al. | 623/34 |
| 2007/0180922 A1 | 8/2007 | Crottet et al. | |
| 2008/0009772 A1 | 1/2008 | Tyler et al. | |
| 2008/0039756 A1 | 2/2008 | Thorsteinsson et al. | |
| 2008/0114272 A1 | 5/2008 | Herr et al. | |
| 2008/0139970 A1* | 6/2008 | Macomber et al. | 600/595 |
| 2008/0147202 A1 | 6/2008 | Danzig et al. | |
| 2008/0200994 A1 | 8/2008 | Colgate et al. | 623/24 |
| 2009/0030530 A1 | 1/2009 | Martin | |
| 2009/0254196 A1 | 10/2009 | Cox et al. | |
| 2009/0287310 A1* | 11/2009 | Fisher et al. | 623/20.21 |
| 2009/0318779 A1* | 12/2009 | Tran | 600/301 |
| 2010/0023133 A1* | 1/2010 | Fairbanks et al. | 623/24 |
| 2010/0131113 A1 | 5/2010 | Even-Zohar | |
| 2010/0249660 A1 | 9/2010 | Sherman et al. | |
| 2010/0249665 A1 | 9/2010 | Roche | |
| 2010/0331733 A1 | 12/2010 | Stein | |
| 2010/0331734 A1 | 12/2010 | Stein | |
| 2010/0331735 A1 | 12/2010 | Stein | |
| 2010/0331738 A1 | 12/2010 | Stein et al. | |
| 2011/0001794 A1 | 1/2011 | Bhanti | |
| 2011/0130684 A1* | 6/2011 | Macomber et al. | 600/587 |
| 2011/0137212 A1 | 6/2011 | Hahn et al. | |
| 2011/0288448 A1 | 11/2011 | Sanders et al. | |
| 2012/0226197 A1* | 9/2012 | Sanders et al. | 600/587 |

OTHER PUBLICATIONS

Boone et al., "Automated fabrication of mobility aids: Review of the AFMA process and VA/Seattle ShapeMaker software design." Journal of Rehabilitation Research and Development vol. 31, No. 1: 42-49, 1994.

Boone et al., "Automated Fabrication of Mobility Aids: Clinical Demonstration of the UCL Computer Aided Socket Design System," Journal of Prosthetic and Orthotics vol. 1, No. 3: 187-190, 1989.

Chan et al., "Dynamic Rectification: A Statistically Based Evolving Socket Rectification Mechanism." 7th World Congress of the International Society for Prosthetics and Orthotics Chicago, IL: 27, Jun. 28-Jul. 3, 1992.

Chan et al., "Surface Curvature Analysis for Enhanced Computer-Aided-Design of Prosthetic Sockets." IEEE 1292-1293, 1993.

Cole et al., "Electrical analogues for tissues." *Experimental Neurology* vol. 24(3): 459-473, 1969.

Commean et al., "Design of a 3-D surface scanner for lower limb prosthetics: A technical note." Journal of Rehabilitation Research and Development vol. 33, No. 2: 267-278, 1996.

Convery et al., "Measurement of the consistency of patellar-tendon-bearing cast rectification." Prosthetics and Orthotics International vol. 27, No. 3: 207-213, 2003.

De Lorenzo et al., "Predicting body cell mass with bioimpedance by using theoretical methods: a technological review." *Journal of Applied Physiology* vol. 82(5): 1542-1558, 1997.

Dean et al., "A Software Package for Design and Manufacture of Prosthetic Sockets for Transtibial Amputees," IEEE Transactions on Biomedical Engineering vol. 32, No. 4: 257-262, 1985.

Donadio et al., "Estimate of body water compartments and of body composition in maintenance hemodialysis patients: Comparison of single and multifrequency bioimpedance analysis." *Journal of Renal Nutrition* vol. 15, No. 3: 332-344, 2005.

Fenech et al., "Extracellular and intracellular volume variations during postural change measured by segmental and wrist-ankle bioimpedance spectroscopy." *IEEE Transactions on Biomedical Engineering* vol. 51, No. 1: 166-175, 2004.

Fuller et al., "Predicting composition of leg sections with anthropometry and bioelectrical impedance analysis, using magnetic resonance imaging as reference." *Clinical Science* London; vol. 96(6): 647-657, 1999.

Gilbert et al., "Effect of frequency, circuit analysis and instrument on extracellular and total body resistance." *Medicine & Science in Sports & Exercise* 672 Suppl: S118, 1995.

Hanai T., "Electrical Properties of Emulsions." In: Sherman P, editor. *Emulsion Science* London, England, Academic Press: 354-477, 1968.

Hastings et al., "Frequency Content of Prosthetic and Orthotic Shapes: A Requirement for CAD/CAM Digitizer Performance." Journal of Prosthetics and Orthotics vol. 10, No. 1: 2-6, 1998.

He et al., "Test of a vertical scan mode in 3-D imaging of residual limbs using ultrasound." Journal of Rehabilitation Research and Development vol. 36, No. 2: 14pp., 1999.

Hoffer et al., "Correlation of whole-body impedance with total body water volume." *Journal of Applied Physiology* vol. 27, No. 4: 531-534, 1969.

Houston et al., "Automated fabrication of mobility aids (AFMA): Below-knee CASD/CAM testing and evaluation program results." Journal of Rehabilitation Research and Development vol. 29, No. 4: 78-124, 1992.

Houston et al., "The VA-Cyberware lower limb prosthetics-orthotics optical laser digitizer." Journal of Rehabilitation Research and Development vol. 32. No. 1: 55-73, 1995.

Johansson et al., "Accuracy and precision of volumetric determinations using two commercial CAD systems for prosthetics: A technical note." Journal of Rehabilitation Research and Development vol. 35, No. 1: 27-33, 1998.

Krouskop et al., "Measuring the shape and volume of an above-knee stump." Prosthetics and Orthotics International vol. 12, No. 3: 136-142, 1988.

Kulczycka et al., "Qualitative and quantitative comparisons of B-spline offset surface approximation method." Computer-Aided Design vol. 34: 19-26, 2002.

Lemaire, E., "A CAD analysis programme for prosthetics and orthotics." Prosthetics and Orthotics International vol. 18, No. 2: 112-117, 1994.

Lemaire et al., "A Quantitative Method for Comparing and Evaluating Manual Prosthetic Socket Modifications." IEEE Transactions on Rehabilitation Engineering vol. 4, No. 4: 303-309, 1996.

Lemaire et al., "Validation of a quantitative method for defining CAD/CAM socket modifications." Prosthetics and Orthotics International vol. 23, No. 1: 30-44, 1999.

(56) References Cited

OTHER PUBLICATIONS

Lilja et al., "Proper Time for Definitive Transtibial Prosthetic Fitting." Journal of Prosthetics and Orthotics vol. 9, No. 2: 90-95, 1997.
Lilja et al., "Volumetric determinations with CAD/CAM in prosthetics and orthotics: Error of measurement." Journal of Rehabilitation Research and Development vol. 32, No. 2: 141-148, 1995.
Matthie et al., "Analytic assessment of the various bioimpedance methods used to estimate body water." *Journal of Applied Physiology* vol. 84(5): 1801-1816, 1998.
McGarry et al., "Evaluation of a contemporary CAD/CAM system." Prosthetics and Orthotics International vol. 29, No. 3: 221-229, 2005.
McGarry et al., "Evaluation of the effect of shape on a contemporary CAD system." Prosthetics and Orthotics International vol. 32, No. 2: 145-154, 2008.
Nyboer J., "Workable volume and flow concepts of biosegments by electrical impedance plethysmography." *T.I.T Journal of Life Sciences* vol. 2(1): 1-13, 1972; Reprinted in *Nutrition* vol. 7, No. 6: 396-408, 1991.
Organ et al., "Segmental bioelectrical impedance analysis: Theory and application of a new technique." *Journal of Applied Physiology* vol. 77(1): 98-112,1994.
Salinari et al., "Bioimpedance analysis: A useful technique for assessing appendicular lean soft tissue mass and distribution." *Journal of Applied Physiology* vol. 94(4): 1552-1556, 2003.
Sanders et al., "A digitizer with exceptional accuracy for use in prosthetic research: A technical note", Journal of Rehabilitation Research and Development, vol. 40, No. 2; Mar./Apr. 2003; pp. 191-196.
Sanders et al., "Assessment of residual-limb volume change using bioimpedance." *Journal of Rehabilitation Research & Development* vol. 44, No. 4: 525-536. 2007.
Sanders et al., "Bioimpedance Analysis and Diurnal Volume Change: Assessment on Trans-Tibial Amputee Prosthesis Users." *Archives of Physical Medicine and Rehabilitation* pp. 1-22, submitted 2008.
Sanders et al., "CAD/CAM transtibial prosthetic sockets from central fabrication facilities: How accurate are they?", Journal of Rehabilitation Research and Development, vol. 44, No. 3; 2007; pp. 395-406.
Sanders et al., "Clinical utility of in-socket residual limb volume change measurement: Case study results." *Prosthetics and Orthotics International* pp. 1-29, submitted 2009.
Segal et al., "Estimation of extracellular and total body water by multiple-frequency bioelectrical-impedance measurement." *The American Journal of Clinical Nutrition* vol. 54(1): 26-29, 1991.
Siconolfi et al., "Assessing total body and extracellular water from bioelectrical response spectroscopy." *Journal of Applied Physiology* vol. 82(2): 704-710, 1997.
Sidles et al., "A quantitative comparison of amputee stump and socket shapes." Proceedings of the 35th Annual Meeting—Orthopaedic Research Society Las Vegas, NV: Feb. 1989.
Sidles et al., "Mathematical techniques for comparing residual limb and sockate shapes." Proceedings of the ISPO Sixth World Congress Kobe, Japan: Nov. 1989.
Sidles et al., "Rectification Maps: A New Method for Describing Residual Limb and Socket Shapes." Journal of Prosthetics and Orthotics vol. 1, No. 3: 149-153, 1989.
Sidles et al., "Rectification Maps: A New Method for Describing Stump and Socket Shapes." In: Davies et al., eds. Report of the ISPO Workshop on CAD/CAM in Prosthetics and Orthotics Seattle, WA; Copenhagen, Denmark; International Society of Prosthotists and Orthotists: 15-18, 1988, 1990.
Smith et al., "Validation of spiral CT and optical surface scanning for lower limb stump volumetry." Prosthetics and Orthotics International vol. 19, No. 2: 97-107, 1995.
Thomas et al., "A comparison of segmental and wrist-to-ankle methodologies of bioimpedance analysis." *Applied Radiation Isotopes* vol. 49, No. 5/6: 477-78, 1998.
Torres-Moreno et al., "A reference shape library for computer aided socket design in above-knee prostheses." Prosthetics and Orthotics International vol. 13, No. 3: 130-139, 1989.
Travis et al., "Computer-aided socket design for trans-femoral amputees." Prosthetics and Orthotics International vol. 17, No. 3: 172-179, 1993.
Van Loan et al., "Use of bioimpedance spectroscopy to determine extracellular fluid, intracellular fluid, total body water, and fat-free mass." *Human Body Composition: in vivo Methods, Models, and Assessment* Edited by: Ellis, New York: 67-70, 1993.
Vannier et al., "Three-Dimensional Lower-Extremity Residua Measurement Systems Error Analysis." Journal of Prosthetics and Orthotics vol. 9, No. 2: 67-76, 1997.
Walsh et al., "A Computerized System to Manufacture Prostheses for Amputees in Developing Countries." Journal of Prosthetics and Orthotics vol. 1, No. 3: 165-181, 1989.
Wotton et al., "Comparison of whole body and segmental bioimpedance methodologies for estimating total body water." *Annals New York Academy of Sciences* 904: 181-186, 2000.
Zachariah et al., "A Method for Aligning Trans-Tibial Residual Limb Shapes So as to Identify Regions of Shape Change", IEEE Transactions on Neural Systems and Rehabilitation Engineering, vol. 13, No. 4; Dec. 2005; pp. 551-557.
Zachariah et al., "Shape and volume change in the transtibial residuum over the short term: Preliminary investigation of six subjects." *Journal of Rehabilitation Research & Development* vol. 41, No. 5: 683-694, 2004.
Zhu et al., "Dynamics of segmental extracellular volumes during changes in body position by bioimpedance analysis." *Journal of Applied Physiology* vol. 85(2): 497-504, 1998.
Zhu et al., "Methods and reproducibility of measurement of resistivity in the calf using regional bioimpedance analysis." *Blood Purification* vol. 21: 131-136, 2003.
Zhu et al., "Validation of changes in extracellular volume measured during hemodialysis using a segmental bioimpedance technique." *ASAIO Journal* vol. 44(5): M541-545, 1998.
Cotton et al., "A Novel Thick-Film Piezoelectric Slip Sensor for a Prosthetic Hand." *IEEE Sensors Journal*, vol. 7, No. 5: 752-761, May 2007.
Chaudhari et al., "Hyperspectral and multispectral bioluminescence optical tomography for small animal imaging." *Physics in Medicine and Biology* vol. 50, No. 23: 5421-5441, Dec. 7, 2005.
Meijer et al., "Method for the measurement of susceptibility to decubitus ulcer formation." *Medical & Biological Engineering & Computing* vol. 27(5): 502-506, 1989.
Meijer et al. "Susceptibility to decubitus ulcer formation." *Archives of Physical Medicine and Rehabilitation* vol. 75(3): 318-323, 1994.
Mein et al., "Skin temperature response to a pressure load: studies in subjects before and during spinal anesthesia." *Archives of Physical Medicine and Rehabilitation* vol. 76(3): 243-245, 1995.
Sanders, J.E., "Thermal response of skin to cyclic pressure and pressure with shear: a technical note." *Journal of Rehabilitation Research and Development* vol. 37, No. 5: 511-515, 2000.
van Marum et al., "Impaired blood flow response following pressure load in diabetic patients with cardiac autonomic neuropathy." *Archives of Physical Medicine and Rehabilitation* vol. 78(9): 1003-1006, 1997.
van Marum et al., "Relationship between internal risk factors for development of decubitus ulcers and the blood flow response following pressure load." *Angiology* vol. 52(6): 409-416, 2001.
van Marum et al., "The relationship between pressure ulcers and skin blood flow response after a local cold provocation." *Archives of Physical Medicine and Rehabilitation* vol. 83(1): 40-43, 2002.
International Search Report and Written Opinion of the International Searching Authority for International Application No. PCT/US2010/022215 mailed on Sep. 29, 2010, 7 pages.
About.com, Grammar & Composition, Definition of "Slash", "/", downloaded from Internet on Sep. 4, 2013, 3 pages.
Restriction Requirement for U.S. Appl. No. 13/193,331 mailed on May 3, 2012, 5 pages.
Non-Final Office Action for U.S. Appl. No. 13/193,331 mailed on Jun. 13, 2012, 10 pages.
Non-Final Office Action for U.S. Appl. No. 13/193,331 mailed on Feb. 26, 2013, 11 pages.

(56) References Cited

OTHER PUBLICATIONS

Final Office Action for U.S. Appl. No. 13/193,331 mailed on Jul. 22, 2013, 11 pages.
Advisory Action for U.S. Appl. No. 13/193,331 mailed on Sep. 18, 2013, 4 pages.
Non-Final Office Action for U.S. Appl. No. 13/193,331 mailed on Feb. 21, 2014, 21 pages.
Notice of Allowance for U.S. Appl. No. 13/193,331 mailed on Sep. 30, 2014, 9 pages.

* cited by examiner

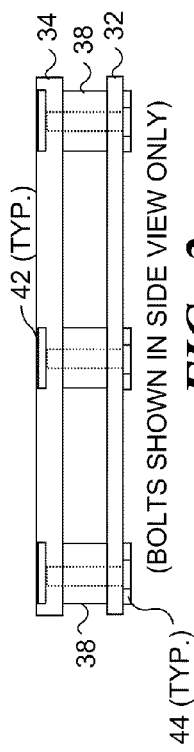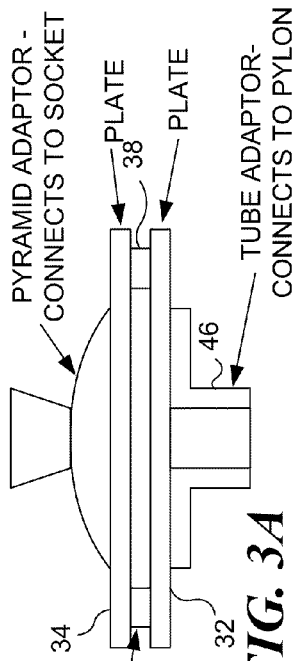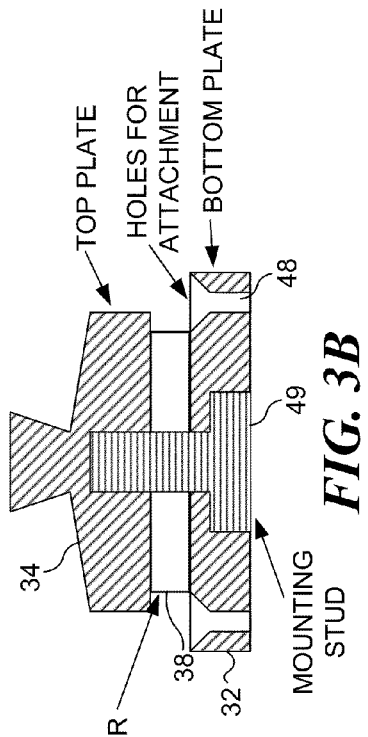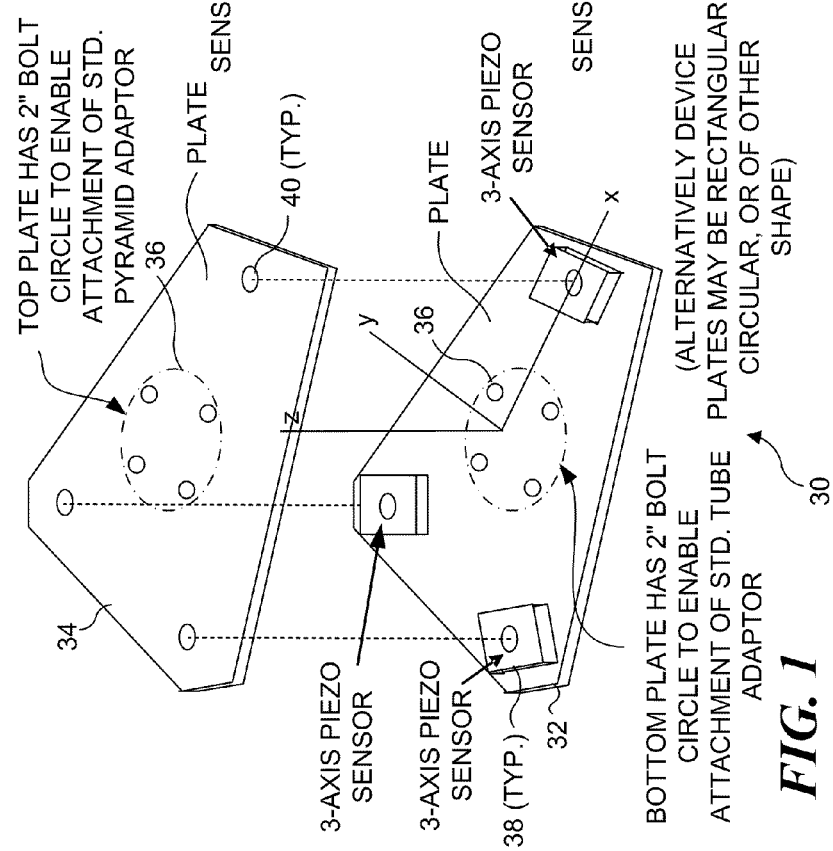

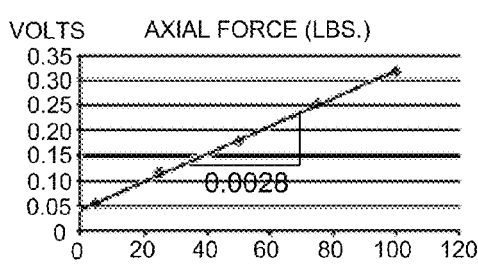
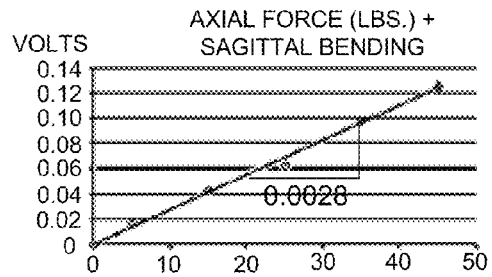
*FIG. 6A*
*FIG. 6B*
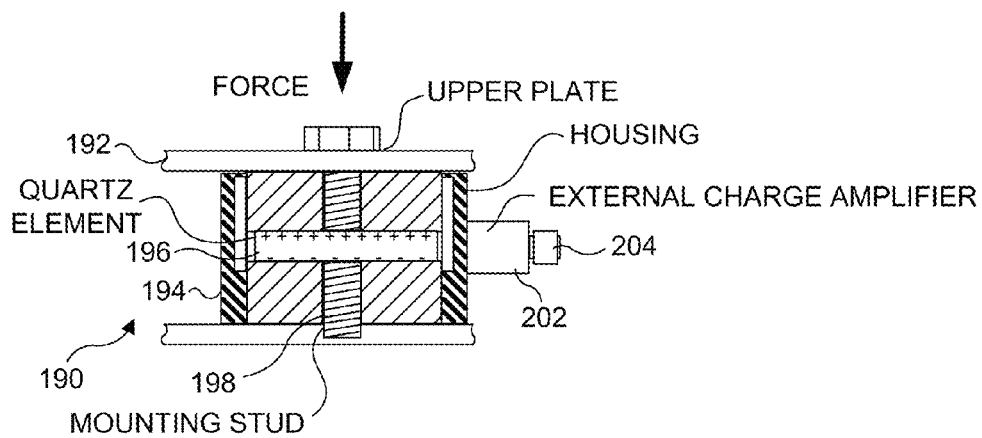
*FIG. 7*
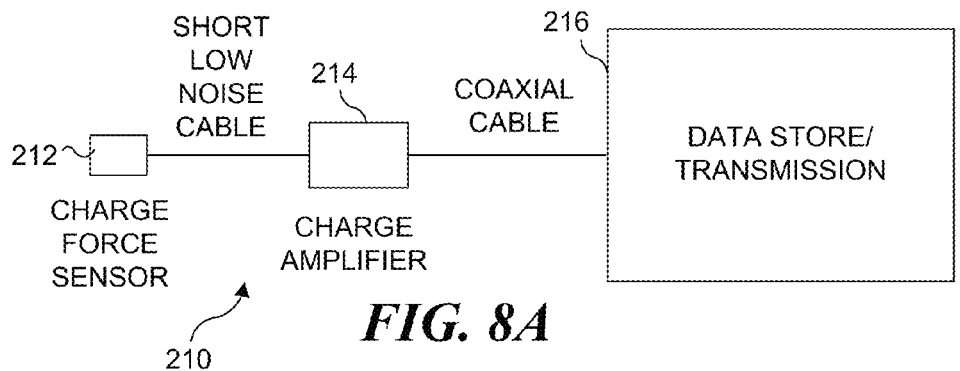
*FIG. 8A*
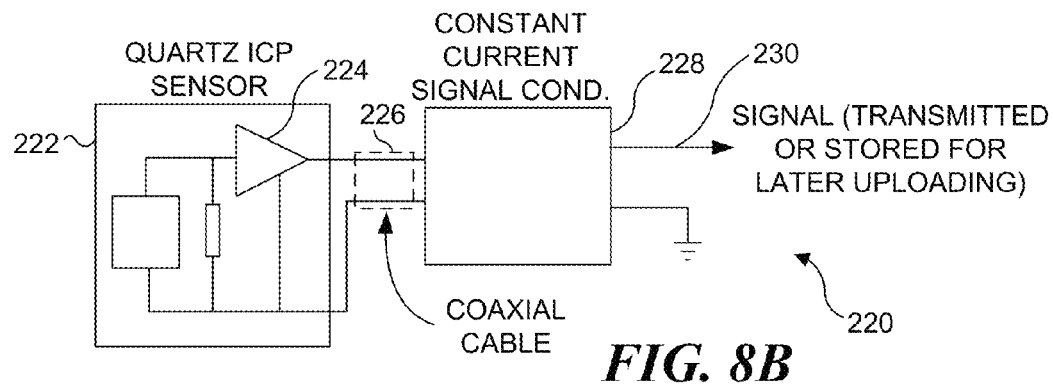
*FIG. 8B*

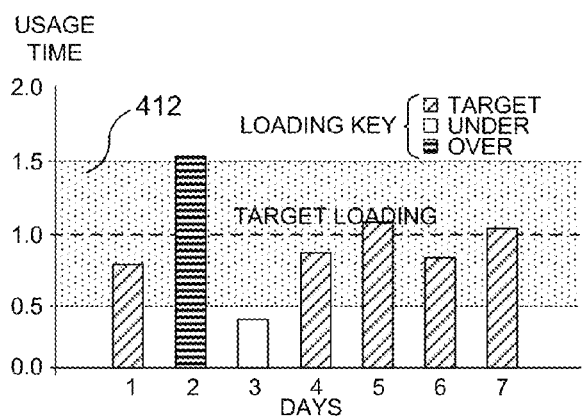
FIG. 17
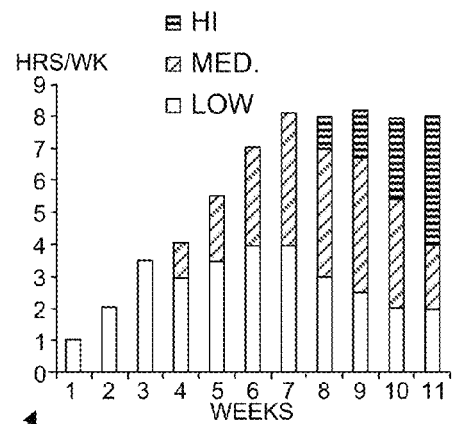
SUMMARY OF STATIC ACTIVITY FOR PATIENT XYZ
FIG. 18
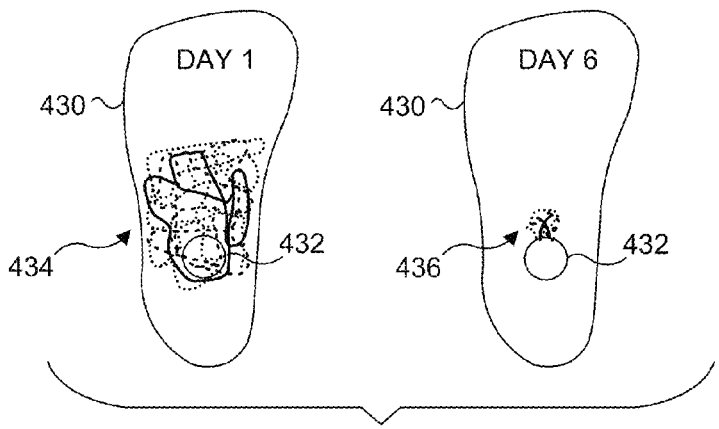
FIG. 19
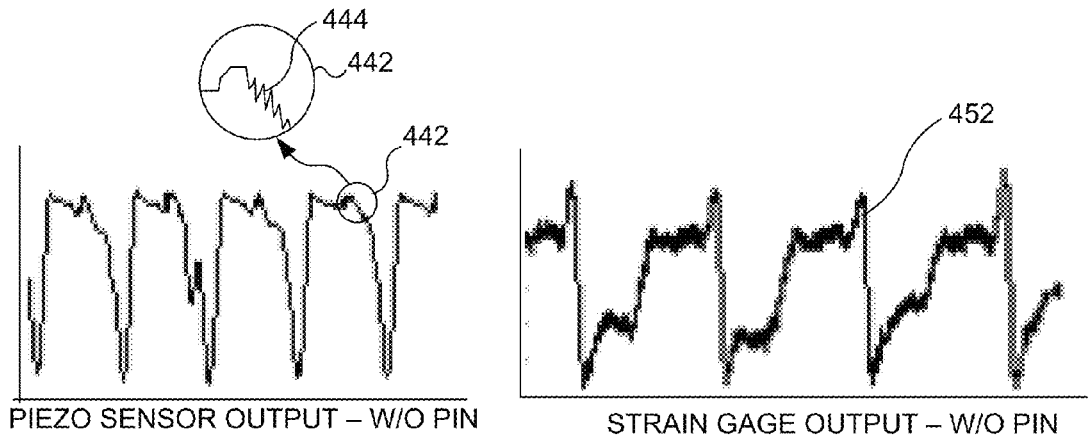
FIG. 20A  FIG. 20B

PROSTHETIC LIMB MONITORING SYSTEM

RELATED APPLICATIONS

This application is based on a prior provisional application Ser. No. 61/147,663, filed on Jan. 27, 2009, the benefit of the filing date of which is hereby claimed under 35 U.S.C. §119(e).

BACKGROUND

The evaluation and assessment of gait, mobility, and activity have become increasingly important to many areas of rehabilitation as the desire and need for evidence-based healthcare continues to grow. Although functional evaluations often rely upon subjective assessments by a clinician or patient self-reports, objective measures have become increasingly preferred for their substantive evidence. Objective evaluation of patient mobility and function, or outcome assessment, is a critical tool for the appraisal of rehabilitation or training programs, justification for an intervention or medical device, or the evaluation of patient activity.

The term "activities of daily living" (ADL) refers to basic functions of everyday life that include such tasks as bathing, dressing, eating, and transferring from one place to another. For most individuals, however, daily activities include a variety of ambulatory tasks such as walking on level ground, maneuvering around corners, moving across inclined or uneven surfaces, and ascending or descending stairs. Participating in a sporting activity can add many other activities such as jumping, running, etc. In this context, true activity is a complex combination of many different biomechanical patterns, occurring randomly throughout the day.

The overwhelming majority of research pertaining to human locomotion has traditionally been conducted in the controlled confines of a gait laboratory, often while subjects move across a level surface, in a straight path. Gait analysis commonly includes the study of kinetics, i.e., forces and moments. This type of study is generally accomplished through the use of a force platform, which is a plate rigidly mounted in the floor of a laboratory for use in measuring applied forces and moments. Computational models enable researchers to extrapolate applied external forces to predict the internal skeletal forces that occur during a gait. While this information has provided researchers with a wealth of information pertaining to how the human body moves through space and how the musculoskeletal structure interacts with the changing momentum of gait, level walking in the laboratory environment encompasses only a small portion of a person's true ADL.

Measuring Real-World Activity

Incline walking has been explored as an alternative to level-ground walking in order to assess the body's response to uneven ground. Evaluation of the kinetic response in incline walking often requires modified instrumentation or unique assessment tools. Researchers have studied kinetics during inclined gait by accurately placing a ramped surface on top of two force platforms. Mathematical modeling was used to resolve the reaction forces and moments on the ramp surface based on the output signals from the platforms. Such a system is an effective laboratory tool, but the size and location of the inclined surface is limited by the placement of the force platforms. In a related recent study, researchers mounted a force platform into an inclined surface to evaluate incline gait dynamics in able-bodied subjects. This solution avoided the need to resolve forces from multiple platforms, but limited observation and analysis to a single step by a subject on the force platform.

Similarly, stair ascent and descent have been researched as an alternative form of gait. Like incline walking, stair kinetics are most often assessed through the placement of strain-gage-based systems, i.e., force plates disposed in stair steps. Such instrumentation has limitations similar to instrumented walkways, since only select steps can be measured and only within the laboratory environment. While such techniques provide effective control of confounding factors, these types of gait may not be truly representative of real-world activity.

Turning gait has also received attention as a potential measure of real-world activity. To date, clinical assessment of turning gait has been derived from qualitative measures or single-step analysis in a gait laboratory. Recently, it has been demonstrated that a rate gyroscope, tethered to a laptop computer, can be used to detect and measure the rate of turning during ambulation in able-bodied subjects. Turns were categorized as soft or corner turns and were identified by a gyroscope voltage output of more than two standard deviations relative to the mean straight-walking reference signal. While such a device holds potential for identifying maneuvering motions in gait outside of a laboratory, the restrictions of a physical tether coupling the device to a computer and the discrimination between only straight or turning gait limit the application of this type of device to only a portion of the true activity domain.

The desire to measure kinetic data during real-world activity with portable instrumentation has been a long standing goal in the biomechanics community. One measurement system that has successfully evolved to record real-world activities is the plantar-pressure measurement system. In this system, thin membrane-like sensors are placed in the insoles of a subject's shoes. Pressure sensors monitor and record the foot plantar pressures during ambulation. Originally, such systems were used to measure only vertical force, were expensive, possessed limited sampling time, and again required direct cabling to a computer. Later systems of this type offered wireless data collection and improved sampling rates, but could acquire continuous data for a maximum time of only a few minutes. Recent commercial systems, such as the Pedar Mobile-X Novel™ (Munich, Germany) offer Bluetooth wireless data collection, have run times of several hours, provide on-board data storage, and exhibit enhanced resolution. Other systems include the Paromed™ (Neubeuern, Germany), Tekscan F-scan™ (Boston, Mass.), and TrueLife SmartFoot™ (Poulsbo, Wash.). Recent studies with these wireless devices have explored the ability to use pressure insoles to resolve the ground reaction force (GRF) by analyzing the pressure data. The estimation required to calculate the anterior-posterior force, especially in periods of double-support, is noted by researchers as a source of error. Additionally, pressure insoles are susceptible to drift, which can cause errors of up to 34%.

Step activity, or the number of steps taken over a given period of time, can be used as an alternative to directly measured forces and moments as an indicator of overall activity. Pedometers and step activity monitors are devices used to measure step activity during ambulation. Research has shown that many pedometers are highly accurate (>90%) for speeds above 3 mph, but become less accurate (<70%) at speeds below 2 mph. For elderly persons or patients with a pathology that can decrease self-selected walking velocity such as a lower-extremity amputation, such devices may not be appropriate Enhanced step monitors, like the Cyma (now Orthocare) StepWatch™ (Mountlake Terrace, Wash.) use uni-axial accelerometers and signal processing to refine the accuracy of step counts. Software settings enable customization of each monitor to a patient, achieving an accuracy of, for example, about 96% (stairs) to about 99% (level walking). Step activity monitors have been used successfully to measure activity in diabetic patients and amputee subjects. However, to date, there has been only limited step activity research applied to evaluate accelerometer-based devices when comparing different types of activities, such as stair ascent or walking on uneven terrain.

Although instrumented stairs/inclines, rate gyroscopes, insole pressure transducers, and accelerometers each offer the potential to reveal a portion of the activity domain, none offer the ability to measure, evaluate, and classify multiple gait activities, which is particularly important for patients with compromised activity levels. One patient group where this limitation is clearly apparent is the amputee population. Loss of a limb can greatly influence the biomechanics of gait and the energy expenditure required for ambulation. For such patients, navigating the terrain of the real world can be challenging. The prosthetic industry has responded to the need of amputees by developing products designed to improve function across a variety of activity domains, including stairs, inclines, uneven terrain, and turns. Energy storage and return (ESAR) feet, microprocessor-controlled knees, shock-absorbing pylons, and rotation adapters are all examples of components designed to accommodate real-world activity domains. Unfortunately, the need for and the function of these devices is limited by only a general understanding of how they are used in the daily lives of amputees. To date, little is known about the types of activities amputees experience in daily life and how those activities influence overall ease with which an amputee is able to participate when using a specific prosthesis.

If real-world activity in the lower-extremity amputee population is to be measured and recorded, a system must be employed that is portable, unobtrusive, and is able to record activity over an extended period of time. Clearly, this requirement effectively eliminates using wires to couple monitoring sensors to a computer or other type of remote telemetry recorder. Furthermore, research is needed to accurately assess the data acquired in order to uniquely identify different types of activity. The objective of such research would be, for example, to identify, quantify, and characterize real-world ambulation in the trans-tibial amputee population. This assessment of and differentiation among real-world activities is critical to understanding prosthetic use and the functional characteristics needed from prosthetic components, devices, and systems. In addition, such a system can be very useful in assessing the proper fit of prosthetic devices to patients. Perhaps more importantly, such research has the potential to create a clinical tool with a wide scope of application—from clinical prescription of a device, to financial justification for an intervention, to the evaluation of a rehabilitation process.

Multiple Axes of Measurement Vs. Selected Axes of Measurement

Although commercial load sensing devices exist specifically for use in amputee prosthetic limbs, none simultaneously and reliably measure both force and moment. In particular, these devices do not measure force and moment well when force is applied in the forefoot, as commonly occurs during the late stance phase of gait. The problem occurs because of crosstalk problems between orthogonal axes of measurement, or between force and moment components of measurement. High bending moments in the sagittal plane tend to distort the force and other moment measures. As a result, interpretation of the force data is limited to conditions where bending moments are low (standing, mid-stance), or exclusively to force, exclusively to moment, or only to selected combinations of force and moment. This issue is relevant in certain application, for example to determine proper prosthetic alignment, since efforts in the 1990's demonstrated that sagittal and frontal bending moments did not predict proper alignment nearly as well as when other components were considered. Thus, a device is needed for use in amputee prosthetic limbs that measures forces and moments reliably across a wide range of loads, and which measures more or all components of force and moment.

SUMMARY

In consideration of the discussion presented above, exemplary apparatus are provided for collecting and processing data indicative of parameters experienced by a prosthesis while a user fitted with the prosthesis engages in activities. The apparatus includes one or more piezoelectric sensors that are attached to the prosthesis to monitor forces experienced by the prosthesis as a result of the user wearing the prosthesis while engaging in the activities. Each piezoelectric sensor develops a charge in response to a force applied to the piezoelectric sensor. For each piezoelectric sensor, an impedance transformation device is included and has a relatively high input impedance and a relatively low output impedance. The impedance transformation device receives the charge developed by the piezoelectric sensor and produces a corresponding output signal indicative of the force applied to the piezoelectric sensor. Also included is at least one data device, which can be either a wireless data transmitter that transmits data comprising the output signals to an external receiver, or a data storage that is coupled to receive the output signal from each impedance transformation device and stores the data comprising the output signal, or a portable processor that accompanies the user while the user engages in the activities and is coupled to receive the output signal from each impedance transformation device. In the latter case, the processor processes the output signal to produce information indicative of the activities in which the user was engaged. This information can be used to detect a problem related to the use of the prosthesis by the user or to adjust a component of the prosthesis.

The data can be transmitted by the wireless data transmitter to the external receiver at the time the data are collected. A network interface is then included to couple the external receiver to a network, enabling the data to be transmitted and processed in real-time at a desired remote location. Also, a data link can be provided for transferring the data from the data storage for processing so as to characterize the activities performed by the user while wearing the prosthesis.

In some exemplary embodiments, the impedance transformation device for at least one piezoelectric sensor is integral within a housing of the piezoelectric sensor.

The impedance transformation device can comprise a charge amplifier, or the apparatus can include a separate charge amplifier to amplify the charge.

The piezoelectric sensor(s) that are included in the apparatus sense components of the force that is applied along a plurality of orthogonal axes. Further, at least one piezoelectric sensor is disposed either proximate to a base of a socket of the prosthesis, or proximate a base of a pylon of the prosthesis, or on a foot portion of the prosthesis. Also, at least one piezoelectric sensor can be provided to produce an output signal indicative of bending of the prosthesis.

The apparatus can also include a plurality of non-piezoelectric sensors that detect a pressure or bending moment and are disposed on the prosthesis in locations appropriate to determine a center of pressure acting on the prosthesis.

Also included is a source of electrical power that provides energizing electrical power. The source of electrical power can include either a kinetic source that responds to movement of the user by producing the electrical power, a thermal source that produces the electrical power in response to a temperature differential between an environment and the user's body, or a chemical source that produces the electrical power as a result of chemical changes that occur while the user is using the prosthesis.

At least one piezoelectric sensor that is provided can include a housing having parallel plates that are sufficiently stiff to resist bending during use when exposed to a range of force likely to be applied to the prosthesis. For example, the parallel plates can be configured as a truss beam, as an I beam, or a honeycomb plate. The outside of at least one plate can include a pyramid adaptor, which is the industry standard for connection and angular adjustment of prosthetic components.

If the data device is either the wireless data transmitter or the data storage, the apparatus can further include a memory that stores machine instructions, and a processor that processes the data in accord with the machine instructions that are stored in the memory. The machine instructions cause the processor to carry out a plurality of functions. These functions include dividing the data (or at least part of the data) into equal intervals of time, so that a duration of the intervals is selected to match features of interest needed to carry out a desired analysis of the data. Another function is determining force components and a plurality of moments acting on the prosthesis, wherein each force component is directed along a different one of a plurality of orthogonal axes. Yet another function is segmenting the data into groups based on the force components and the plurality of moments. Relative to the prosthesis and in regard to a magnitude of a force and a moment applied to the prosthesis, the processor also characterizes the groups of data based on a desired scheme, to represent a plurality of biomechanical events.

The machine instructions can further cause the processor to determine a location for a center of pressure on a portion of the prosthesis, and to determine the plurality of moments acting on the prosthesis based on the force components and the center of pressure.

Also, the machine instructions can further cause the processor to automatically prepare a report for the user and/or a medical practitioner. The report presents the results achieved by characterizing the groups of data based on the desired scheme, so as to represent the plurality of biomechanical events and qualities of those individual biomechanical event groups.

In at least some exemplary embodiments, each piezoelectric sensor, each impedance transformation device, and each data device are included as integral parts of the prosthesis.

Another aspect of the present approach is directed to a method for collecting, processing, and employing data indicative of kinetic parameters experienced by a prosthesis while a user fitted with the prosthesis engages in activities. The method includes the step of attaching one or more piezoelectric sensors to the prosthesis to monitor forces experienced by the prosthesis as a result of the user wearing the prosthesis while engaging in the activities. As noted above, each piezoelectric sensor develops a charge indicative of a kinetic parameter experienced by prosthesis. The charge produced by each piezoelectric sensor is conditioned, producing a corresponding output signal indicative of the parameter experienced by the prosthesis. The output signal from all piezoelectric sensors is then used to produce the data indicating the kinetic parameters. The data are processed to determine the kinetic parameters experienced by the prosthesis and for evaluating conditions related to use of the prosthesis by the user.

The method can further include the step of wirelessly transmitting the data from the prosthesis to either a local site, or a remote site, where the step of processing the data is carried out. Also, some embodiments include the step of transmitting the data to a remote site over a network.

The step of processing can include the step of characterizing the activities that are carried out by the user while wearing the prosthesis. The data can comprise two or more parameters selected from a group of parameters. The group includes a component of force directed along one of a plurality of orthogonal axes, a moment relative to at least one of the plurality of orthogonal axes, an indication of the prosthesis bending, and an indication of at least one parameter on a foot portion, such as a resultant force position, a direction that a force is applied, and a center of pressure. Also included in the group of parameters is an indication of a position where a shear force is applied to the prosthesis, a temperature of a portion of the prosthesis, a velocity of the prosthesis as the user moves about, an angle of the prosthesis, and a force inside a socket of the prosthesis.

The method can also include the step of supplying electrical energy to energize the one or more piezoelectric force sensors and other components used for collecting the data by harvesting energy as a result of the activities in which the user engages while wearing the prosthesis. The step of harvesting energy can be implemented by using a force resulting from the user engaging in activity to provide an input to a piezoelectric generator, producing an electrical output current, or using a temperature differential developed between a portion of a body of the user and an environment to generate the electrical output with a Peltier device, or by using a chemical gradient developed due to a chemical change that occurs as a result of the activity of the user within one of a tissue of the body of the user, and a material of the prosthesis. Energy can also be transferred to energize the components using electromagnetic induction, as discussed below.

In addition, the method can include the step of communicating the data to an automatically adjustable component of the prosthesis. The data can then be used for automatically adjusting the component to more effectively fit the prosthesis to the user, in regard to the activity of the user.

Further, the method can include the step of automatically activating collection of the data when the user is at a specific predefined location where the user engages in a training session. The data that were automatically collected can then be processed to provide either a medical practitioner or the user with information about a progress of the user in the training session.

The step of processing the data can include the steps of preparing and presenting a report showing information derived from the data, to provide feedback to the user about a condition related to the use of the prosthesis by the user, to monitor changes in user health, or how the person is adapting to the prosthesis. The information comprising the report can be presented to the user on a device that is readily accessible by the user.

Also, the step of processing the data can include the steps of automatically identifying a pattern for an activity being performed by the user, and detecting whether the activity places the user at risk of injury. If so, the method can include the steps of warning the user that the activity identified is placing the user at risk of injury, and/or automatically adjusting a component of the prosthesis to reduce a risk of injury to the user as a result of the activity recognized.

The step of processing the data can also include the step of providing information for enabling a medical practitioner to determine if the user is either overusing or underusing the prosthesis, or is at a risk of an injury, when engaging in one or more activities.

The data can be processed to provide information for enabling a medical practitioner to determine if components used in the prosthesis are appropriate to fit the user properly or should be changed to better fit the user in connection with the activities in which the user has been engaging.

The step of processing the data can include the steps that are generally consistent with the functions implemented by the processor discussed above.

The method can also include the step of using the data with a model to predict either where and/or when soft tissue breakdown will occur as a result of use of the prosthesis by the user. The data can also be used with a model to assess an alignment of components of the prosthesis and to determine any change that should be made to correct a problem with the alignment. The method can also include the step of employing results of the step of processing the data to determine if the activities in which the patient engages are cause for changing the prosthesis or a component of the prosthesis used by the patient, or to advise the patient to alter his or her activities for medical reasons.

While most of the following discussion is directed to lower limb prostheses, it should also be understood that the same approach can also be applied to upper limb prostheses. It is therefore not intended that the apparatus or method disclosed herein be limited to a prosthetic device fitted to a specific portion of a patient's body.

This application specifically incorporates by reference the disclosure and drawings of the provisional patent application identified above as a related application.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 is an exploded isometric schematic view of an exemplary embodiment showing components of a monitoring device in accord with the present approach, in which two generally parallel plates are configured to be attached between a socket and a prosthetic pylon (in this embodiment) so that a plurality of piezoelectric force sensors can be employed to detect three-axis loads, as measured between the plates, producing data that can subsequently be accessed for evaluation, as discussed below;

FIG. 2 is a side elevational view of the exemplary embodiment for the components of the monitoring device of FIG. 1, illustrating a plurality of threaded fasteners (in cross-section) that connect the upper plates together on opposite sides of the 3-axis piezoelectric sensors;

FIG. 3A is a side-elevational view of the exemplary embodiment shown in FIGS. 1, 2, illustrating the pyramid adaptor that connects to a patient socket and a tube adaptor that connects to a pylon of a prosthesis;

FIG. 3B is a schematic side-elevation view of the exemplary embodiment shown in FIGS. 1, 2, and 3A, but includes only one piezoelectric sensor instead of multiple sensors;

Figures 5A, 5B:
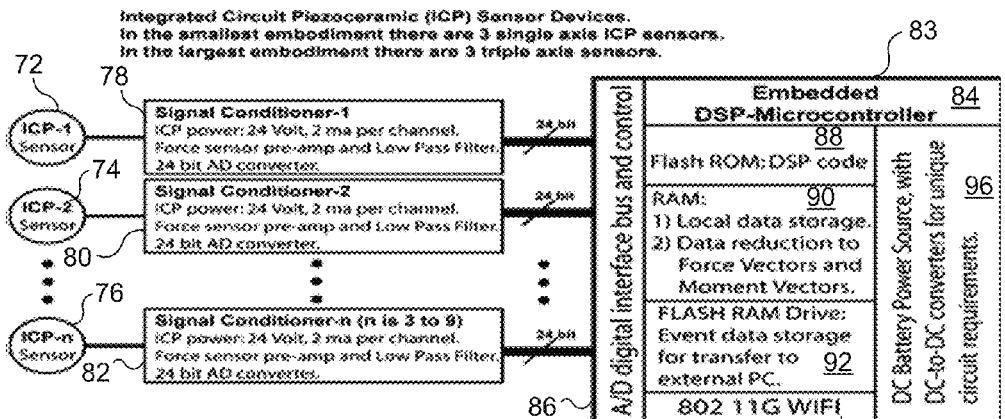
Figure 5C:
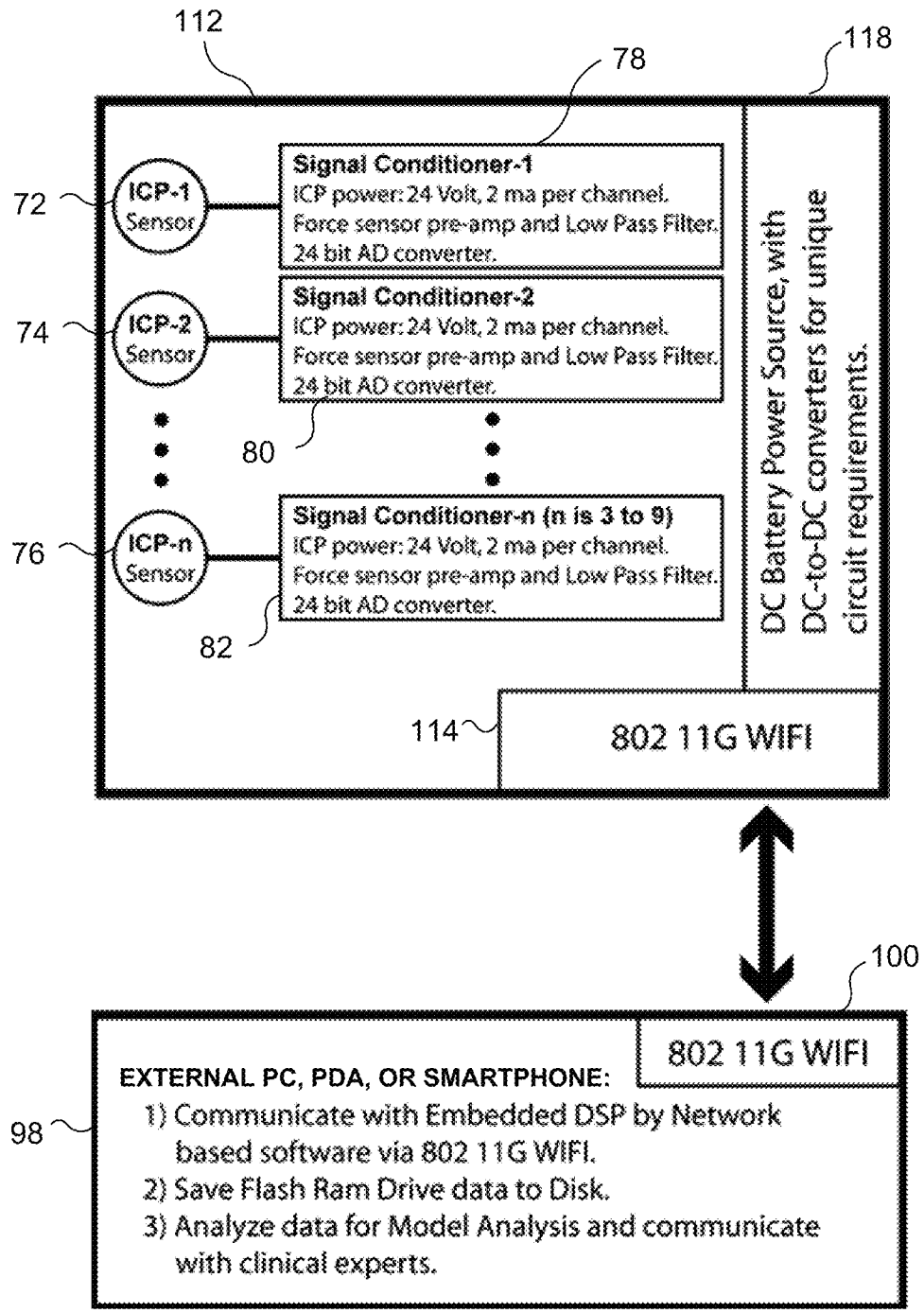
Figure 9A:
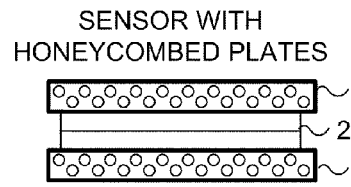
Figure 9B:
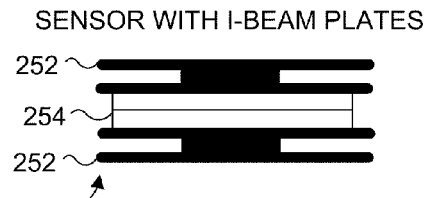
Figure 10:
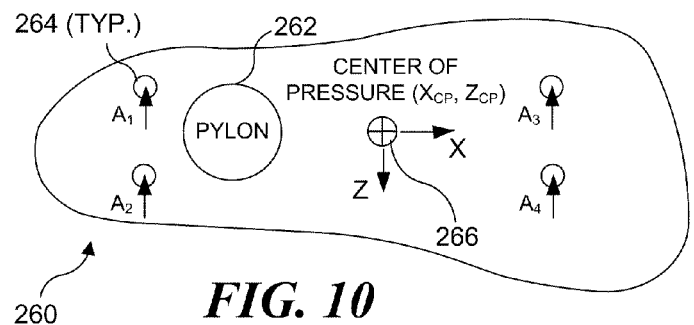
Figure 11A:
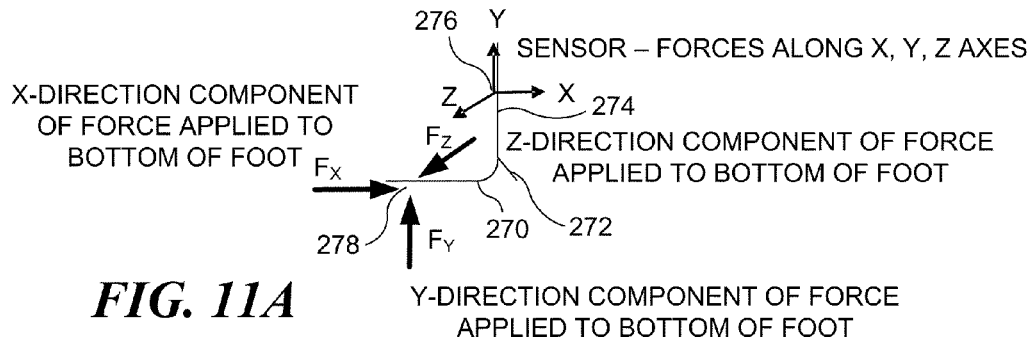
Figure 11B:
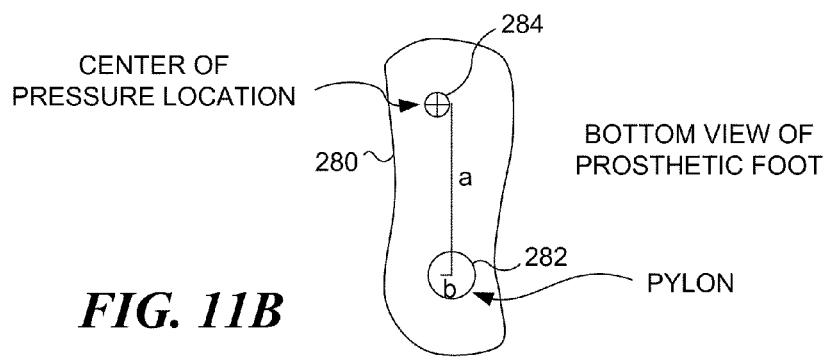
Figure 12:
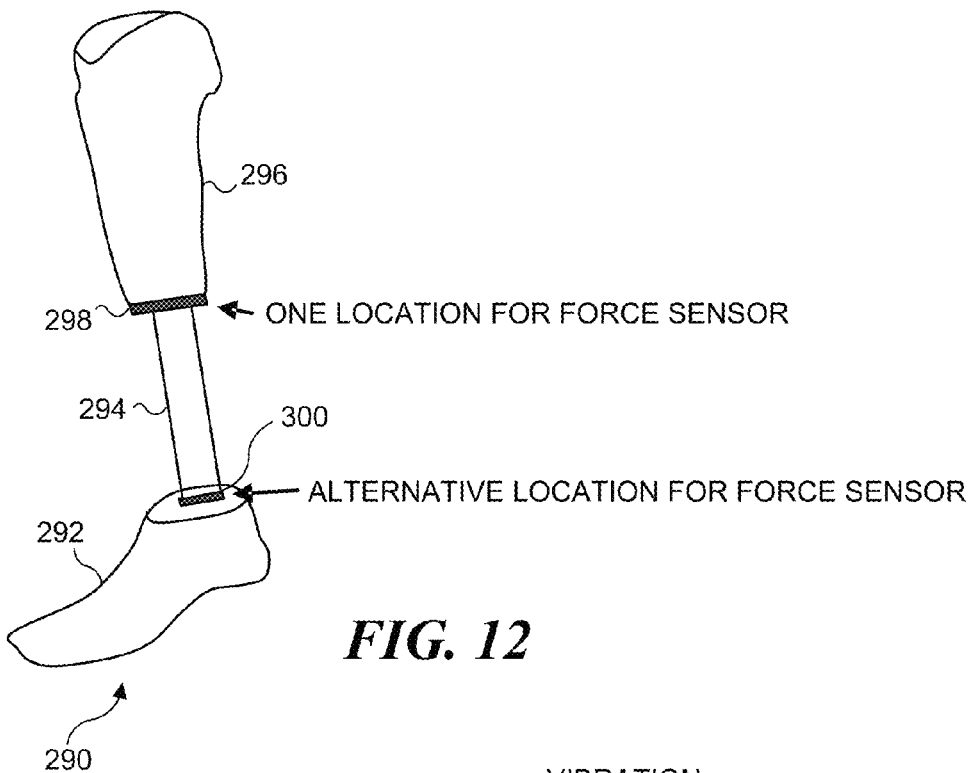
Figure 13A:
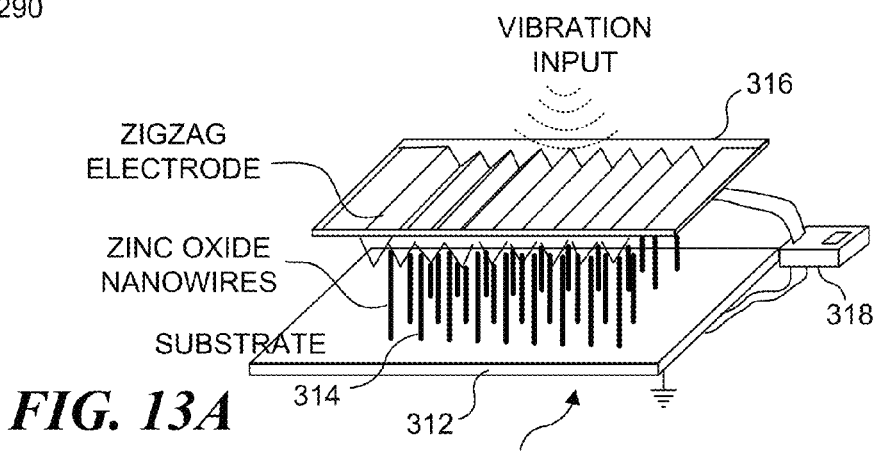
Figure 13B:
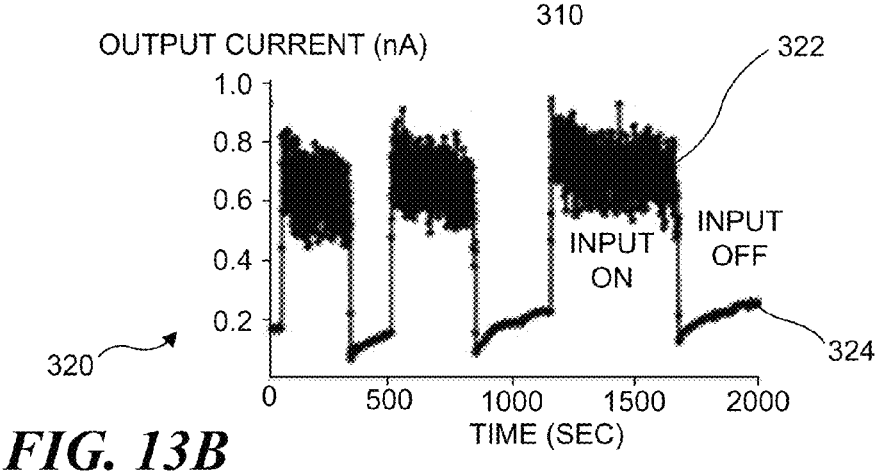
Figure 14:
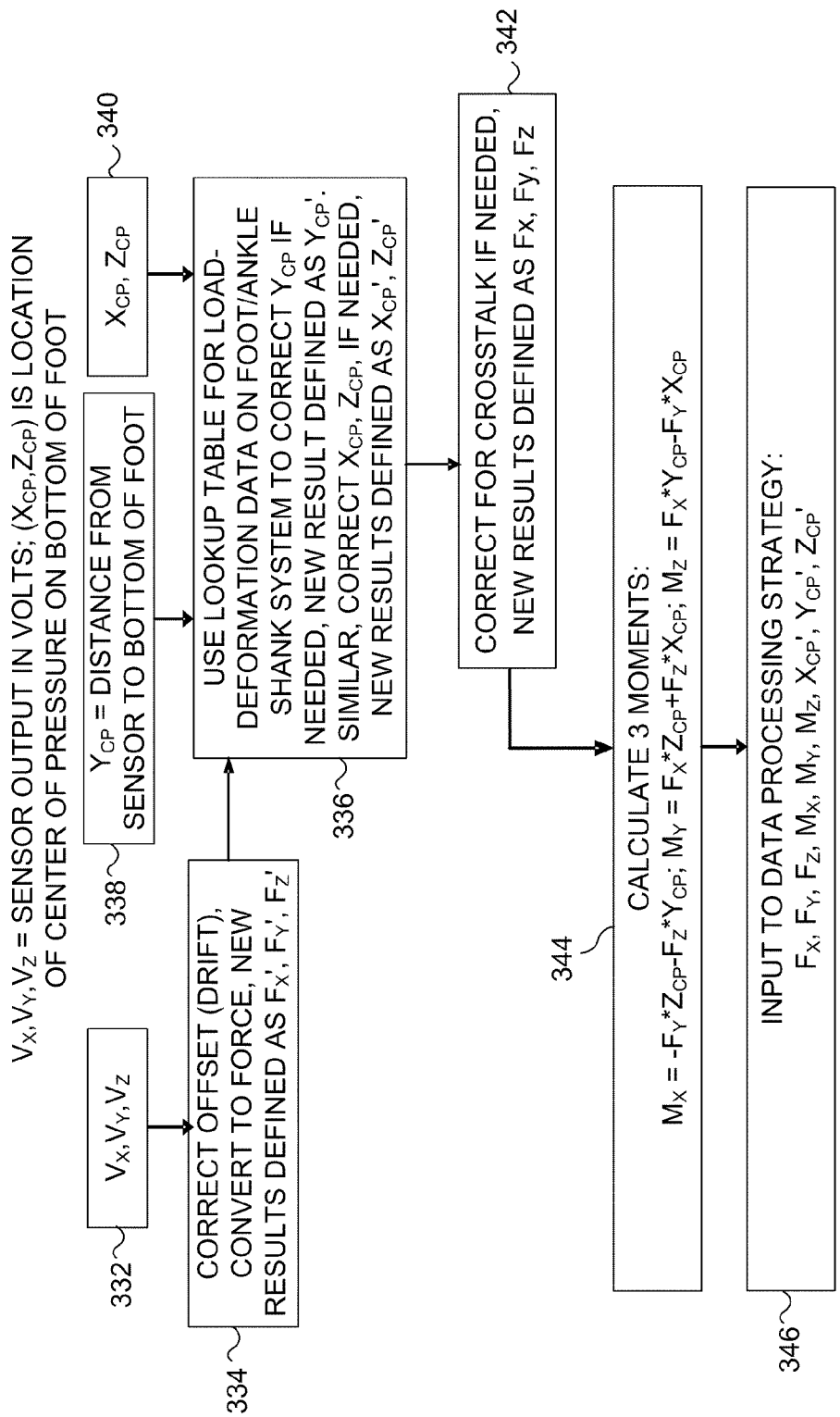
Figure 15:
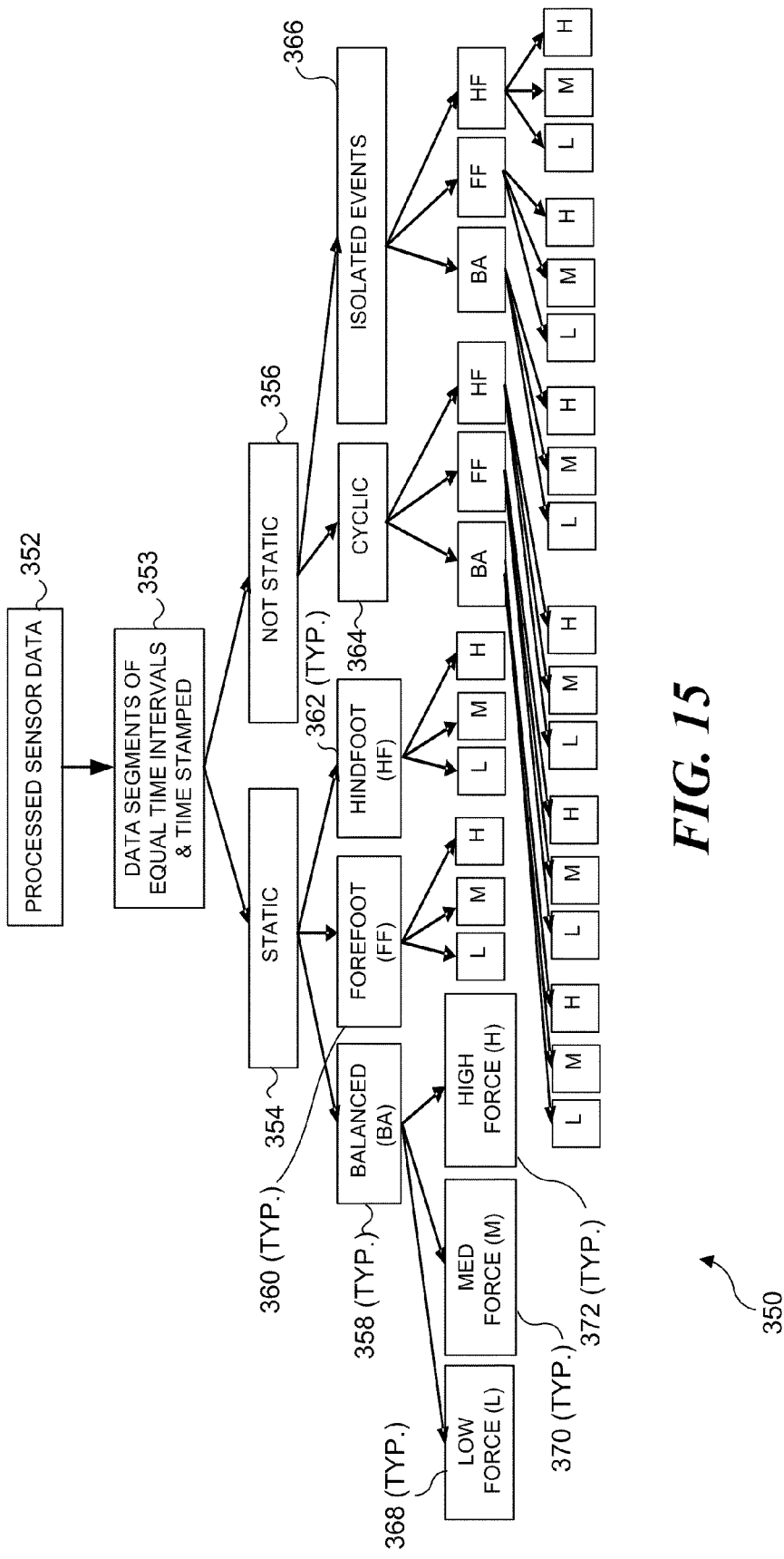
Figure 16:
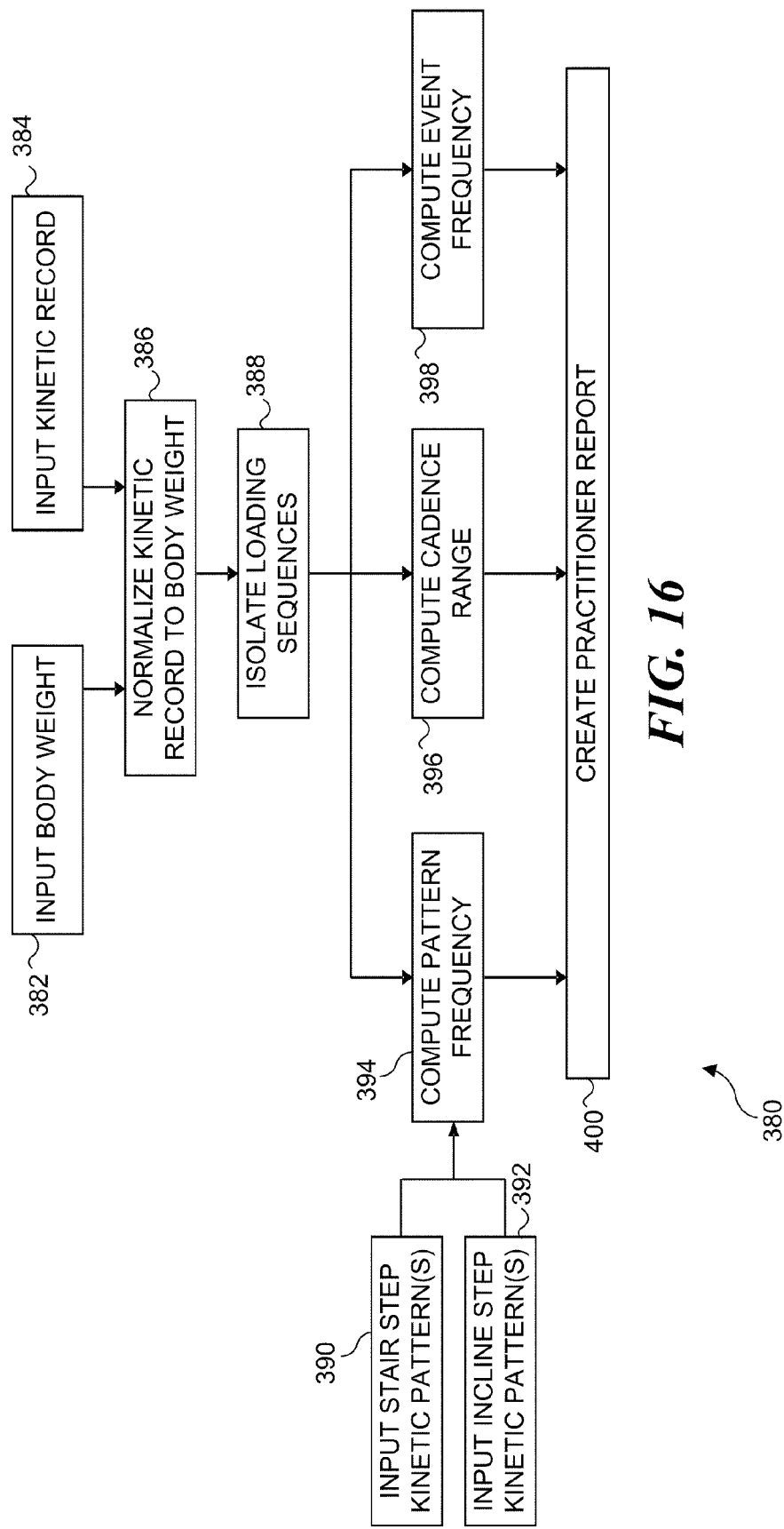
Figure 21:
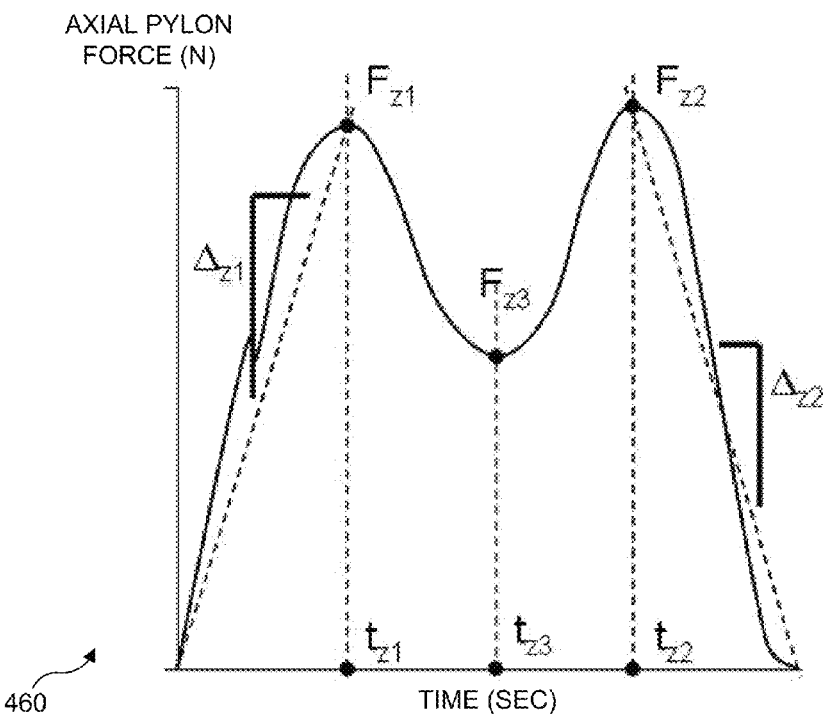
Figure 22:
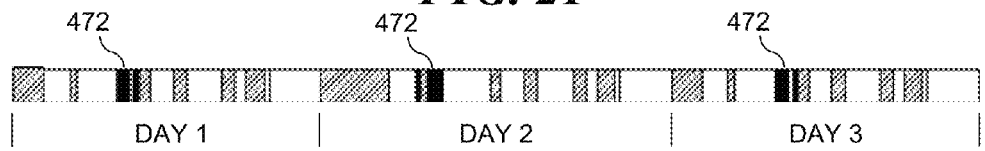
Figure 23:
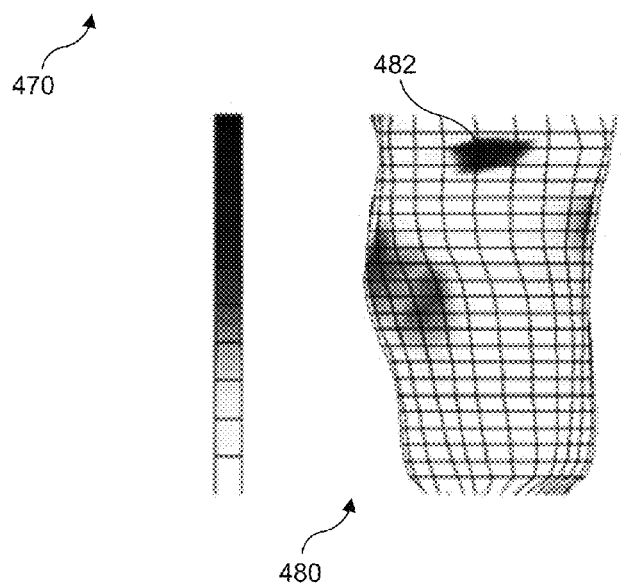

FIGS. 5A, 5B, and 5C are functional block diagrams of three exemplary alternative configurations of the kinetic monitoring system for collecting data from a plurality of piezoelectric sensors, for example, the 3-axis piezoelectric sensors shown in FIGS. 1-3;

FIGS. 6A and 6B are, respectively, a graph showing axial force vs. force sensor output voltage when axial force is exclusively applied, and a graph showing axial force vs. force sensor output voltage when both axial force and a sagittal bending moment are applied;

FIG. 7 is a simplified cross-sectional view of an exemplary piezoelectric dynamic force sensor that includes an external charge amplifier disposed immediately adjacent to the sensor housing, such as a piezoelectric sensor selected from the Ring Force Series 201/261™ sensors that are available from PCB Piezotronics Inc., which is suitable for use in connection with monitoring dynamic forces experienced by a prosthesis during ADL;

FIG. 8A is an exemplary block diagram illustrating a piezoelectric charge force sensor, charge amplifier, and data store (or real-time data transmission) component, for use in monitoring dynamic forces experienced by a prosthetic device;

FIG. 8B is a drawing derived from product literature obtained from PCB Piezotronics, Inc. that illustrates an alternative approach to that shown in FIG. 7, wherein an integrated circuit piezoelectric (ICP) sensor includes a quartz (or ceramic) charge sensor that is integral with a charge amplifier in a common housing, to further minimize charge leakage that might occur in the configuration of FIG. 7, enabling the output signal produced to be applied through a conventional coaxial cable (or two wire conductor) to a constant current signal conditioner, to provide an output signal either for transmission in real-time to an external processor, or for storage and subsequent downloading to an external processor;

FIGS. 9A and 9B are schematic cross-sectional views of piezoelectric sensors respectively with honeycombed and I-beam plates, so that the relatively stiff plates provided thereby resist bending when a load is applied;

FIG. 10 is a plan view of the bottom of an exemplary prosthetic foot, showing how a plurality of piezoresistive sensors, capacitive sensors, or pressure cells disposed there can be employed (in combination with the piezoelectric dynamic force sensor), to determine the center of pressure and force acting on the foot at that point;

FIG. 11A illustrates a force diagram in connection with a schematic view of an exemplary prosthetic foot, to show how the piezoelectric dynamic force sensors are used with the center of pressure measurement to determine the location of the three orthogonal components of dynamic force experienced by the prosthesis;

FIG. 11B is a simple plan view of the bottom of an exemplary prosthetic foot, illustrating the distances "a" and "b" that are used in the determination of the center of pressure location;

FIG. 12 is an isometric side view of an exemplary prosthesis showing two alternative locations for mounting the piezoelectric force sensors that are used in the present approach for monitoring force acting on the prosthesis;

FIG. 13A is an isometric schematic view of an exemplary energy harvesting nanowire electrical generator that has been developed by Zhong Lin Wang, Director of the Center for Nanostructure Characterization at the Georgia Institute of Technology, showing one type of device that can be used on a prosthesis to generate electrical current for powering the electronic components used for monitoring and collecting data;

FIG. 13B is an exemplary graph showing the output of the nanowire generator of FIG. 13A vs. time;

FIG. 14 is a flowchart showing exemplary logical steps for processing the data collected from monitoring a prosthesis to determine kinetic information;

FIG. 15 is a block diagram illustrating an exemplary data classification scheme to process the data from FIG. 14 so that the collected data are segmented into groups based on the force and moment applied to the prosthesis;

FIG. 16 is a flowchart illustrating further exemplary steps for using the data classification of FIG. 15 to create a practitioner report;

FIG. 17 is a graph illustrating exemplary daily loading data monitored for a prosthesis using the present approach, for presentation to a person wearing the prosthesis, or to a practitioner;

FIG. 18 is a graph illustrating an exemplary weight-bearing progression for a new prosthesis patient over 11 weeks of wearing a prosthesis for increasing (at least initially) periods of time;

FIG. 19 illustrates a plan view of a prosthetic foot, respectively showing an exemplary initial postural sway on the left side of the Figure, and after five days on the right side of the Figure, based on data collected using the present approach;

FIGS. 20A and 20B are respectively graphs of a piezoelectric sensor output signal and a strain gage output signal for a prosthetic socket in which the locking pin has been removed from the liner so that there is slippage, which illustrates that a resulting high frequency perturbation is evident in the piezoelectric sensor signal—but not in the strain gage signal;

FIG. 21 is an exemplary graph of axial pylon force (N) for a prosthetic device, as a function of time in seconds, illustrating how the force data can be analyzed to identify features of the biomechanical force experienced by a patient that might indicate problems or monitor status, in accord with the present approach;

FIG. 22 is an exemplary bar graph of data collected over a three-day period indicating (i.e., the repeating solid black intervals) where high magnitude force activities occurred repetitively during the period; and FIG. 23 is a grayscale graph illustrating an exemplary computational finite element model result wherein the darker patches indicate stresses (in the normal direction) on a residual limb (in psi), where the grayscale range is from 0.0 to 8.7 psi.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Overview of the Benefits of the Present Prosthetic Monitoring System and Method

The exemplary monitoring system, with its associated hardware and software discussed below, is a tool intended to collect data for use in assessing and monitoring conditions experienced by a lower-limb amputee patient who is using a prosthesis. Because it is fully portable and not tethered by a wire to fixed data collection/processing devices, the kinetic monitoring system is capable of collecting data outside of a laboratory setting, enabling this monitoring system to serve as an innovative tool for prosthetic assessment and treatment. By providing biomechanical information about prosthesis performance outside the clinic, during a patient's daily activities and routine, the device provides the medical practitioner with quantitative information never before available. Such information should enable a practitioner to adjust a prosthesis to better accommodate the real world needs of the patient. Further, it is contemplated that the kinetic monitoring system can be coupled to appropriate automatic adjustment apparatus disposed within (or connected to) the prosthesis, so that such adjustments can readily be performed in an automated fashion without even involving the practitioner.

Overview of Use of the Monitoring Device

FIGS. 1, 2, and 3 illustrate an exemplary plate and piezoelectric sensor configuration 30 that can be used for a monitoring system in accord with the present approach. In this embodiment, a lower plate 32 is coupled to an upper plate 34, with three 3-axis piezoelectric sensors 38 disposed about a 2" bolt circle 36 disposed proximate the center of plates 32 and 34. The upper and lower plates are coupled to opposite sides of piezoelectric sensors 38 by threaded mounting studs 42 that extend through orifices 40 and through the piezoelectric sensors that are thus mounted between the two plates, using threaded nuts 44 that are tightened on the threaded mounting studs.

A practitioner conducting a fitting or refitting of a patient with a prosthesis installs the kinetic monitoring system within the prosthesis. Because this exemplary embodiment of plate and piezoelectric mounting configuration used in the kinetic monitoring system has a standard pyramid shape adaptor 40 on the top and a 2" bolt circle on the bottom, illustrated as connecting to a tube adaptor 42 in the exemplary embodiment of FIGS. 3A and 3B, it easily connects between the shank (or foot if there is no separate shank) and socket portions of the patient's prosthetic limb—which is only one of the possible locations for mounting the force sensors; alternative locations are discussed below. In FIG. 3B, another exemplary configuration is illustrated where only one 3-axis sensor is used, and the upper part of the top plate is in the shape of the standard pyramid adaptor used in the industry. A pyramid adapter is a device installed in the prosthesis that connects socket, shank, foot or other prosthetic limb components together such that it allows angular adjustment of the two components. The bottom plate is configured with the standard 2" bolt circles holes 48 for attachment. A mounting stud 49 extends through the piezoelectric sensor and couples the upper and lower plates together. The device can be installed in this configuration or upside-down with the pyramid adapter towards the foot. Further, it should be understood that other types of connectors can instead be used, since the industry standard 2" threaded fastener circular configuration is used in this exemplary embodiment.

Use of the Kinetic Monitoring System

Figure 4:
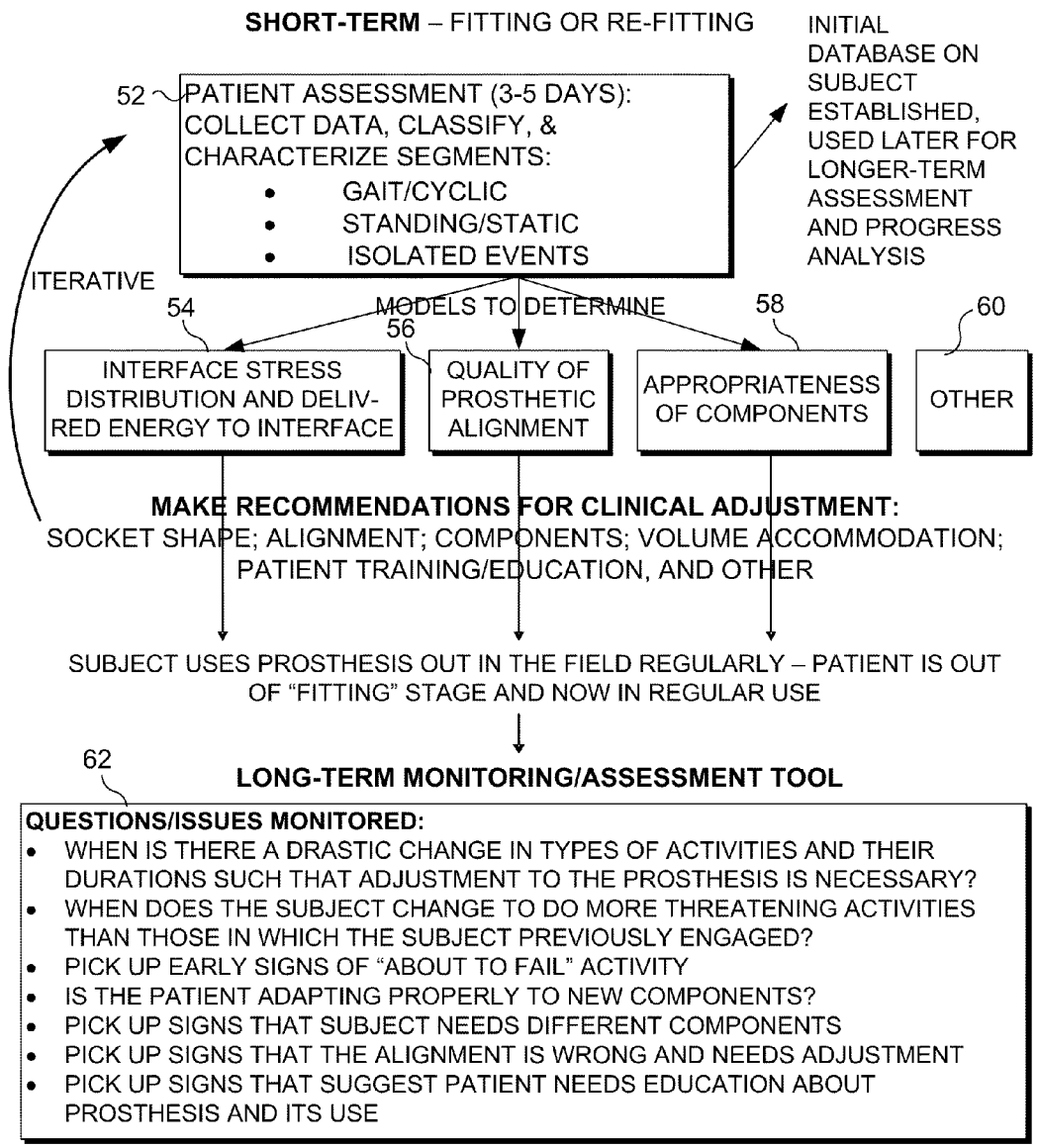
FIG. 4 is a functional description of how the present monitoring device might be used in connection with a prosthesis provided to patients who have experienced a limb amputation.

The following discussion is illustrated in a block diagram 50, in FIG. 4. Based upon the duration of data collection, there are at least two uses for the kinetic monitoring system, one short term and one long term. As indicated in a block 52, in the short term use, the monitoring device remains coupled to the prosthesis for a period ranging, for example, from a few hours to several days, while the patient carries out his or her normal activities and routines.

At present, three analytical models indicated in blocks 54, 56, and 58 are envisioned to process the data (but other models, as indicated in a block 60 can also be employed). These models provide crucial information for the practitioner that cannot be determined by other means. The first model indicated in block 54, uses inputs from the collected data to determine the soft tissue breakdown risk. It identifies if and/or where the tissues are being overstressed, both in terms of magnitude and duration of load application in terms of interface stress distribution and the energy delivered to the interface. In short, the model in block 54 predicts if and where the soft tissues are going to break down. The second model in block 56 assesses the quality of the alignment of the prosthesis, determining if the alignment is set correctly or incorrectly and what changes should be made to fix it if it is incorrectly aligned. This second model uses either a strategy similar to early 1990's work using neural network/fuzzy logic analysis, a roll-over shape technique under development at Northwestern University, a force-time integral approach, or a customized work/energy technique developed for this application.

The third model in block 58 assesses the appropriateness of the components of the prosthesis being used by the patient based upon the type and intensity of the patient's activity. Key clinical problems, such as matching the appropriate type of prosthetic foot, ankle, and/or pylon to the patient are addressed with this model. Other models are under development, such as that for optimizing liner selection and volume accommodation devices. One or more other models are contemplated, once a database has been established and it is possible to generate "standard curves" for different out-of-lab activities. For example, another model might compare new patient data with those curves and identify clinically relevant abnormalities.

From the models, recommendations are made for clinical adjustment. Adjustments include modifications of the socket shape, alignment, prosthetic components, volume accommodation, vacuum-assist settings, and suspension, as well as determining the need for additional patient training/education. The information provided by the prosthetic limb monitoring system will prompt the practitioner to bring the patient into the clinic and adjust the prosthesis for optimal use by the patient, thereby enhancing function and performance of the prosthesis. Retesting will then likely be conducted.

In regard to its long term use, the device is employed for an extended time monitoring tool for the patient. Particularly for high risk patients, the device serves as a useful and effective monitoring tool of patient health. A number of issues and questions are assessed, as indicated in a block 62 and as noted below:

Does the patient undergo a drastic change in types of activities and/or duration of activities such that limb injury is a concern?
Does the patient undergo changes in activities such that prosthesis adjustment or clinical attention is required (e.g., a component is broken or fatigued)? Is the fatigue life of the components being approached?
Is the patient adapting to the new prosthesis or adjusting to new settings appropriately?
Is the patient demonstrating problems with balance and may the patient be at risk for an adverse event, such as a fall?
Is the patient in need of new or different types of prosthetic components?
Is the patient in need of adjusted alignment in the prosthesis?
Does the patient require clinical education, gait training, or physical therapy to properly use the prosthesis in environments outside of the clinic space?

The preceding questions and issues arising in the long term monitoring and assessment of a patient using the kinetic monitoring system are intended to be only exemplary and not in any way limiting. Just as was done for the short term, analogous models can be developed for long term monitoring to answer these and many other questions. Also, it is contemplated that the long term monitoring can collect data that can provide feedback to control automated components, such as a volume controlled socket liner that will automatically be adjusted to meet the needs of the patient as the patient engages in different daily activities.

Functional Block Diagrams—Exemplary Embodiments of Kinetic Monitoring System

Three exemplary embodiments 70, 110, and 120 of the kinetic monitoring system are illustrated respectively in the functional block diagrams of FIGS. 5A, 5B, and 5C. In each of these embodiments, signal conditioners 78, 80, and 82 are disposed to couple to the output signals from the n piezoelectric sensors 72, 74, and 76, which are mounted between the plates (not shown in these Figures).

In exemplary embodiment 70 in FIG. 5A, the conditioned output signal is coupled through wire connectors to a processing pack 83, which may be disposed in a box mounted to the prosthesis or carried on a waist belt. Processor pack 83 receives the conditioned output signal with an analog-to-digital (A/D) interface and control 86. An embedded digital signal processor (DSP) microcontroller 84 implements preprocessing of the data supplied from the signal conditioners. Also included in processing pack 83 are a flash read-only memory (ROM) 88, a random access memory 90, a flash RAM drive 92, an IEEE 802.11g WiFi transceiver 94, and a direct current (DC) battery power source with DC-to-DC converters 96. Further details of the function of each of these components of the processing pack are discussed below.

Data processed by processor pack 83 is conveyed wirelessly by IEEE 802.11g WiFi transceiver 94 to an IEEE 802.11g WiFi transceiver 100 in an external personal computer (PC), personal data assistant (PDA), or smartphone 98, for further processing. It should be noted that the reference to these computing devices (i.e., PC, PDA, or smartphone) is intended to be exemplary and not in any way limiting of the type of device that can implement further processing and analysis of the data, and/or display reports based on the data, since it is contemplated, that almost any type of programmed logic computing device or hardwired logic device might be used for this purpose. For example, the further processing and analysis of the data might instead be implemented on an application specific integrated circuit (ASIC), or on other types of computing devices that execute software programs, such as a server, a laptop, or a netbook computer.

In contrast to the wired connection between the signal conditioners and processing pack in exemplary embodiment 70 of FIG. 5A, exemplary embodiment 110 in FIG. 5B comprises a sensor assembly 112 that includes an IEEE 802.11g WiFi transceiver 114 for wirelessly transmitting the conditioned sensor output signal to IEEE 802.11g WiFi transceiver 94 in processing pack 83. Sensor assembly 112 also includes a DC battery power source with DC-to-DC converters 118 to provide electrical power to the sensor assembly. Thus, in this exemplary embodiment, it is not necessary to provide a cable between the sensor assembly disposed on the prosthesis and the processing pack, which may also be located on or in a different portion of the prosthesis or carried by the user of the prosthesis at some other convenient location. In exemplary embodiment 110, a telemetry system (wireless) can be used to transport the data from the prosthesis to processing pack 83 on a waist pack or pocket pack, and to transmit the data to a portable or fixed computing device, or to a nearby data storage. The data storage (such as an electronic memory device) as well as means for communication over the Internet to a base or host computer can be disposed within processing pack 83 on a waist pack or pocket pack, or included with the prosthesis. Also, other types of wireless communication can be used, such as Bluetooth, other types of 802.11 WiFi protocols (without any intended limitation) can be used instead of the IEEE 802.11g communication used in these examples.

In exemplary embodiment 120 shown in FIG. 5C, processing pack 83 is not used. Instead, sensor assembly 112 communicates the conditioned output signals directly to a base computer such as external personal computer (PC), personal data assistant (PDA), or smartphone 98 wirelessly, and the processing software or logic executed on the base or host computing device (or hardwire logic device) can be used for all of the processing and analysis of the data that are produced by the piezoelectric sensors.

The following discussion provides further details about the components and various aspects of the exemplary embodiments of the kinetic monitoring system shown in FIGS. 5A, 5B, and 5C.

Piezoelectric Force Sensors

A number n of either 1, 2, or 3 axes piezoelectric force sensors 72, 74, and 76 are employed. For example, piezoelectric force sensors from PCB Piezotronics that have low drift and minimal crosstalk are suitable for use in this application. All of the exemplary embodiments 70, 110 and 120 use ICP sensors that include a charge amplifier in the housing of the force sensor, to minimize drift and charge decay. Alternatively, instead of multi-axis force sensor(s), a plurality of single axis force sensors can be employed that measure along parallel axes.

Single 3-Axis Sensor Vs. Multiple 3-Axis Sensors or Multiple 1-Axis Sensors

The advantage of using a single sensor in monitoring a prosthesis rather than multiple sensors is that a single sensor is smaller, more lightweight, and less energy consuming. A single 3-axis sensor measures forces in three orthogonal directions. Piezoelectric technology is particularly appropriate for measurement of these forces because the crosstalk between orthogonal directions of measurement is minimal in certain commercial piezoelectric devices (e.g. PCB's 260™ piezoelectric series). Further sensitivity of the force measurements to simultaneously applied bending moments, particularly in the plane of the axial force, is minimal. It might be that for some clinical applications sufficient information is derived from the single force sensor alone measuring in three orthogonal directions. However, for applications where additional information is needed (e.g., to determine moments, and center of pressure location), the additional information can be determined using data from the single 3-axis sensor in combination with other sensors. For example, with measurement of the location of the center of pressure, e.g., measured on the bottom of the foot using existing commercial piezoresistive, capacitive, or pressure cell sensor technology, coupled with measurement from the single 3-axis sensor, the three moments (sagittal bending, frontal bending, torsion) can be calculated, as described below. Strain-gage fasteners with a strain-gage like those currently available commercially are also applicable. Alternatively, by using a bending sensor (e.g., a strain gage sensor, a piezoresistive sensor, a piezoelectric sensor) coupled with measurement from the single 3-axis sensor, moments in the measured directions can be determined, and the location of the applied force in the prosthesis can be determined in at least one plane.

The advantage of using multiple 3-axis sensors is that all force and moment components are measured directly by the sensor, and the resultant force location is easily determined. No additional sensor is needed. The calculation of forces is achieved through summing the measured forces from the multiple sensors in each of the three orthogonal directions. Moments are determined by calculating the location of the resultant force, which can be done using the data from the multiple 3-axis sensors. This is done through quasi-static analysis by developing equations via summation of all moments to zero for each of the three orthogonal directions. By multiplying the force component by the distance to the appropriate axis determined by calculating the location of the resultant force, each of the moments is determined.

The use of multiple single axis sensors provides a reduced cost, but at the expense of limited data. At most, only one component of force and two moments can be determined using multiple single axis sensors. For example, axial force, sagittal bending, and frontal bending can be measured. Research using such devices has been carried out since the early 1990's.

Signal Conditioners

Low-power signal conditioners 78, 80, and 82 running at 24 V and 2 mA per sensor and having 24 bits of resolution are used in each of these exemplary embodiments. Depending on the specific piezoelectric sensor used and the resolution needed for clinical purposes, these characteristics can readily be changed as necessary. In FIG. 5A, ICP force sensors 72, 74, and 76 provide an output signal to the input of n corresponding signal conditioners 78, 80, and 82.

Microcontroller

In exemplary embodiments 70 and 110 of FIGS. 5A and 5B, a digital signal processor (DSP) microcontroller 84 embedded in processing pack 83 reduces the conditioned data to force and moment vectors. Flash ROM 88 stores embedded DSP code used to control processing of the conditioned data, and RAM 90 provides local data storage and is used for data reduction to obtain the force vectors and moment vectors (discussed below). Flash RAM drive 92 is used to store event data for subsequent transfer via IEEE 802.11g WiFi transceiver 94 to a corresponding IEEE 802.11g WiFi transceiver 100 on a portable or fixed base or host computing device, such as external PC, PDA, or smartphone 98, for further processing.

The data collected in flash RAM drive 92 and transmitted to the external PC, PDA, or smartphone 98 (or other portable or fixed base or host computing device) are saved to disk after being received. The model approach discussed above, or another data processing paradigm is applied by external computing device to process the data for storage and further analysis, and preparation of one or more reports for presentation to the user of the prosthesis and/or to clinical medical practitioners. Software enhancements can also be downloaded from the external computing device to DSP microcontroller 84 in processing pack 83.

Appropriate models can be employed for the clinical applications of the kinetic monitoring system described herein. The piezoelectric sensors used in the kinetic monitoring system should sample the piezo output signals at a relatively high rate (e.g., more than 120 samples/sec, which is considered high for gait analysis) because of the need to properly capture high frequency events. However, it is only necessary to store the data, which show these events, at that high rate; other data for events that do not need to be captured at a high rate will be captured at a lower rate, or can be stored at a lower rate, for example, by decimating the data before storing. Thus, one function of the microcontroller in exemplary embodiments 70 and 110 of FIGS. 5A and 5B is to assess the data coming from the piezoelectric sensors through the signal conditioners and decide at what intervals the data should be stored. The microcontroller will also place the kinetic monitoring system into a sleep mode when there is no activity by the user, to save power. The microcontroller can also control data transfer from storage to a remote computing device, via the wireless transmitter.

Power/Battery and Energy Harvesting

Energy harvesting technology can be incorporated in the kinetic monitoring system in order to use the power generated while the user is walking or while the user engages in other forms of activity, to energize the kinetic monitoring system and/or to charge any of DC battery power sources 96, and 118. For example, a scaled-up version of the nanogenerators developed at the Georgia Institute of Technology can be employed. In these nanogenerators, a wire is displaced within a magnetic field by the mechanical action of the prosthesis during use, inducing current in the wire. Energy from that unit can be used to operate the device, as well as to charge a battery for use when the patient is less active. Until this technology is sufficiently enhanced to meet all the power needs of the device, lightweight batteries, and a plug-in recharger can instead or also be used, so that the unit can be re-energized overnight. Potentially, a non-cabled recharging technology (e.g., a charger like that developed by Intel Corporation) could instead be used and might charge a super capacitor instead of a battery. Other options for energy harvesting to provide electrical power to energize the kinetic monitoring system are discussed below.

For example, non-cabled or telemetry wireless power recharging capabilities are currently under development by Intel Corporation and others that may be used to provide electrical power to the components of the kinetic monitoring system. By employing user-generating power devices such as those being developed at the Georgia Institute of Technology, it is envisioned that a kinetic monitoring system can be produced that is completely maintenance free for the patient and practitioner, since it will not require frequent battery replacement. As a further alternative, the system battery power supply might be recharged during the evenings or at night when the patient is asleep. Alternatively, when patient activity is low, the device can be energized with power stored in a battery that was user-generated during periods of patient activity. The kinetic monitoring system can transmit data over the Internet on command, without any attention or intervention being required of the user. Analysis and reporting to the clinician is thus completely automated. The host computer can be equipped with software to process and clinically interpret the data.

Data Storage

Flash RAM drive 92 (in exemplary embodiments 70 and 110 of FIGS. 5A and 5B) serves as a data logger for intermediate storage of data until the data are transferred to non-volatile memory (such as a hard drive) in external PC, PDA, or smartphone 98, or 146, other host or base computing device. Numerous examples of solid-state memory devices or portable hard drives are readily available for this purpose.

Wireless Transmitter Via E-Net

As noted above, a portable device such as a PDA or smartphone, but perhaps even simpler and more compact, can be used to download the data collected by the sensor assembly of the kinetic monitoring system and also can transfer the data to a remote site for further processing. For example, when commanded by embedded DSP microcontroller 84, the portable PDA, smartphone, or other computing device can connect to a specified Internet (or other network) address via a local area network (LAN) or wide area network (WAN), or over the Internet, and then download data from the data storage unit to the remote computer or other computing device at the designated IP address. If communication cannot be established, the microcontroller can keep a record of the amount of data that are in the storage unit and energize a "data storage near to full" LED on the front of the portable device such as a PDA or smartphone, to indicate that the data logger is approaching its maximum storage capacity. In an early exemplary embodiment, data are transferred directly to a host or base PC using a commercial digitizer with WiFi (or alternatively, Bluetooth or other wireless protocols can be used for this purpose).

As shown in FIGS. 5A, 5B, and 5C, the exemplary embodiments of the kinetic monitoring system collect force and moment data from the prosthesis based on the output signals from a plurality of piezoelectric force sensors (e.g., three single axis, one 3-axis, or three 3-axis, such as piezoelectric sensors 72, 74, and 76). Optionally, other types of data can be collected from other sensors (not shown) that are included on or proximate to the prosthesis. For example, it is contemplated that acceleration data (collected using one or more accelerometers) and angulation data might be collected. Data are collected by the piezoelectric sensor(s) at a high sampling rate so that impulsive events are accurately recorded by the kinetic monitoring system. Optionally, an on-board computer can be provided as part of the monitoring system to process the data and store only relevant information that is collected when the patient is actually engaged in an activity or is not quiescent. For example, if a patient stands for an extended period with minimal changes in forces or moments experienced by the prosthesis, the kinetic monitoring system can store data at a relatively low sampling rate, thereby consuming less memory storage for the data collected, and using less electrical power. This technique will thus save both physical and memory space, and electrical power. When the prosthesis is not moving for extended periods, the kinetic monitoring system can enter a sleep mode so as to further conserve power. Power consumption is an important operating parameter, since all power is supplied by on-board batteries, or alternatively, by harvesting energy derived from the activity of the user, or from temperature differentials, or based on chemical changes to make use of otherwise wasted energy. The electrical current produced by energy harvesting can be used for recharging the battery (or to energize the system if sufficient electrical power is being harvested so that a battery is not needed).

In some exemplary embodiments, the kinetic monitoring system includes a telecommunication system so that collected data are periodically sent (for example, 1-2 times/day) to the practitioner's clinic (or other remote site) for analysis. Software at the remote site segments the data into cyclic, standing, and "isolated event" categories, with further sub-categorization depending on the analysis being conducted, as further discussed below. The intent is to classify activities and track the duration of different activities, thereby providing information that by itself is useful to a medical practitioner for optimizing the prosthetic prescription. However, the collected and derived information can also be further post-processed using novel analytical models discussed below in order to perform advanced gait analysis, predict or detect at-risk activities, and inform the medical practitioner and/or user, to enable better decisions—both in the clinic and during use of the prosthesis.

The kinetic monitoring system also has potential application as a monitoring tool for amputee soldiers who have returned to duty out in the field, as well as other potential military applications. It also has potential use as a research tool for companies to better design their prosthetic components. In addition, such a device can be used as the sensing unit of a control system to manually or automatically adjust a prosthesis in real time so as to maximize its performance. Applications include sports, military, and recreational use of prosthetic limbs. It can also be used with a vacuum-assist feedback control system to manually or automatically adjust vacuum level, or with a volume controlled liner or socket to automatically adjust the volume.

The kinetic monitoring system will also be helpful for mechanical standards development in the field. Little is known about amputee activity levels outside the lab. Issues such as fatigue and suggested replacement schedules can be developed using the data derived by monitoring real world activities by amputees.

A fuzzy logic system for gait pattern recognition and analysis might be incorporated into the system, making clinically relevant decisions to adjust the prosthesis appropriately. Adjustments include socket shape, alignment, components that should be used, and other design features. With this technological approach, the practitioner's expertise is mimicked in the software within the device.

In concept, the kinetic monitoring system can be mounted at the ankle between the pylon and foot or at another location between the socket and ground, which might be more convenient for the user. It could be mounted within a direct skeletal attachment device, as well.

It might be beneficial to have different piezoelectric force sensor designs for different applications or subject groups, such as a sports sensor, a child sensor, or an adult sensor.

The piezoelectric force sensor can help to establish a patient's activity level as applied to selection of the components of the monitoring device, thus potentially providing the justification to medical insurers that the monitoring device is necessary.

Exemplary embodiments of the kinetic monitoring system can work with an on-board telemetry transmission system, such as IEEE 802.11g WiFi transceivers 94, 100, and 114, to wirelessly transmit data to a nearby or geographically remote stationary computer or to a portable computing device, such as processor pack 83, which is carried by the patient on or in the prosthesis or within a waist-belt or pocket pack, if needed. Alternatively, the kinetic monitoring system can include electronic or magnetic memory media such as flash RAM 92 to retain data that can subsequently be uploaded to a host computer through a wire connector (e.g., a universal serial bus link) at convenient times when the patient is in the same location as the host computer. Or, periodically, the data retained in the flash RAM memory of the device can be uploaded to the host or base computing devices via a wireless link such as Wi-Fi, or Bluetooth, as noted above.

During mounting of the kinetic monitoring system to a patient in the clinic, a separate computing device that communicates with the kinetic monitoring system can record the prosthesis components used so that the start date of activity with each component is recorded. The separate computing device can thus assess how much and how long each component is used, which can assist in determining when it is appropriate to replace a specific prosthesis component due to wear. Instrumentation As discussed above, exemplary embodiments of the kinetic monitoring system can use 3 (or 4) spaced-apart stacks of piezoelectric sensors to monitor force and moment in from one to three orthogonal directions, or a single stack for force in three orthogonal directions. The number of sensing directions employed depends on how many of the force and moment directions applied to the socket are deemed necessary to monitor, for specific clinical applications.

Although the kinetic monitoring system adds length to the prosthesis where it is disposed, the length is easily accommodated by simply shortening the pylon, which is a minor adjustment. An advantage of the present kinetic monitoring system over much of the prior art sensor technology is that it uses standard modular components for collecting, processing, and storing data produced by the piezoelectric force sensors.

It is important to understand that the piezoelectric force sensors used in measuring dynamic force and other parameters in the present kinetic monitoring system differ from more conventional piezoresistive sensors and are not accelerometers (although accelerometers often use piezoelectric materials and have been used in prosthetics). An accelerometer has a mass within it (which can be simply the mass of the piezoelectric material itself) that is deflected in response to the acceleration applied in a designated direction. The mass experiencing the acceleration applies force to the piezoelectric material within the sensor, causing a change in its electrostatic charge, which can be detected. The configuration of the piezoelectric sensors used in the present exemplary approach for sensing dynamic force and other parameters is different in that it does not have a mass within the sensor that responds to acceleration. Instead, the piezoelectric sensor responds to a force that is applied directly to the piezoelectric material from outside the piezoelectric sensor.

Also, the piezoelectric sensors used in the present approach should be pre-loaded. The piezoelectric sensor is pre-loaded between two relatively stiff plates, using a bolt (usually at least partly made of copper) that connects the top and bottom plates and passes through the centers of the piezoelectric material disks. In contrast, accelerometers are not pre-loaded. Pre-load is important in the piezoelectric sensors used in this application, not only to enable the piezoelectric sensor to respond to dynamic force, but also to enable force measurements in both directions (e.g., so that the piezoelectric sensor can respond both to tension and compression applied to the two plates along a designated sensing axis).

Pre-loading also makes the piezoelectric sensor more linear in performance than when not pre-loaded. In other words, pre-loading makes the piezoelectric sensor more linear when the force is not at the extremes of its measurement range.

In the present application in a prosthesis, pre-loading also helps to solve the challenging sagittal bending moment crosstalk problem that makes design of a prosthesis force sensor challenging. The difficulty is that when a person uses a prosthetic limb, there is a high bending moment in the sagittal plane during walking, and the bending occurs late in the stance phase when the resultant force on the foot is centered out towards the toes. That bending moment tends to distort the axial force measurement because it is of relatively high magnitude. The high aspect ratio of the piezoelectric sensor crystals and the high pre-loading helps to minimize this problem in this type of sensor. The pre-load also helps to make the piezoelectric materials in this configuration relatively insensitive to bending.

FIGS. 6A and 6B are graphs that respectively illustrate the calibration test results for a prototype of a piezoelectric force sensor. In both Figures, the vertical axis is voltage in volts and the horizontal axis is axial force in lbs. Only axial force along the central axis of the sensor is applied in a graph 180 in FIG. 6A. Both axial force and sagittal bending, with an applied bending moment of up to 21 ft-lbs, are applied in a graph 182 in FIG. 6B. The slopes (voltage vs. axial force) of the line shown in these graphs for calibration under axial load are comparable to those for axial load with sagittal bending, meaning that the sensor is minimally sensitive to crosstalk from an applied sagittal bending moment. Similar results were obtained when shear forces or torsional moments were applied. Linearity with minimal crosstalk was also observed in these other measurements obtained from the sensor.

Note that in the ICP sensor, the impedance transformation device (e.g., a charge amplifier) is an integral component disposed within the housing of the piezoelectric sensor. Alternatively, the impedance transformation device can be disposed immediately next to the housing of the piezoelectric sensor, as shown in an exemplary piezoelectric sensor 190 in FIG. 7. This exemplary piezoelectric sensor is coupled to an upper plate 192 by a mounting stud 198, which is threaded into the lower plate, but not into housing 194. Mounting stud 198 provides the required pre-load, as discussed above. As shown for piezoelectric sensor 190, the impedance transformation device (i.e., a charge amplifier 202) should be as close as possible to piezoelectric material 196 and housing 194 so as to reduce charge leakage that might occur in a short length of even a very high impedance cable. A relatively low impedance coaxial cable can be coupled to an output connector 204.

FIG. 8A illustrates a configuration 210 in which a piezoelectric sensor 212 develops an electrical charge in response to an applied force. A charge amplifier 214 (or other impedance transformation device) must be coupled by a very short low noise cable to the piezoelectric sensor (i.e., be disposed adjacent to the sensor housing), to avoid unacceptable charge leakage in the cable. However, the output signal from charge amplifier 214, which has a very high input impedance, but a relatively low output impedance, can be coupled through a conventional coaxial cable or two conductors, to a data store or transmission device 216, since the charge amplifier isolates the charge on the piezoelectric sensor from the low impedance coaxial cable. To even further reduce charge leakage, a configuration 220 (shown in FIG. 8B) includes an ICP sensor 222 that has an integral charge amplifier 224 within it. ICP sensor 222 can be coupled through a conventional coaxial cable 226 to a constant current signal conditioner 228, which produces a conditioned output signal conveyed on a lead 230 for transmission or storage.

It is not essential that the impedance transformation device used with piezoelectric sensors amplify the signal (i.e., it need not be an amplifier); instead, it just needs to have a very high input impedance with a much lower output impedance. Accordingly, a charge amplifier with these characteristics can also be used as the impedance transformation piezoelectric sensor. In an alternative embodiment (not shown) of the piezoelectric sensor in which an internal impedance transformation device is disposed within the piezoelectric sensor housing, the charge or voltage amplifier can be separate and disposed at some distance away from the piezoelectric sensor.

The piezoelectric sensor is housed within a frame configured so that the plates disposed on opposite sides of the sensor are parallel to each other when the piezoelectric force sensor is assembled and do not bend during use. Plate bending would deteriorate performance of the piezoelectric sensor. Making sure that the piezoelectric materials do not experience bending is thus very important in this application of the force sensor. The reason this is so important is because in this application, there is so much potential for bending as a result of a force being applied far out on the toe of the foot relative to the disposition of the pylon of the prosthesis. However, it is also important to reduce mass so that the sensor unit does not add undo weight to the prosthesis. FIG. 9A illustrates a piezoelectric sensor 240 that includes honeycombed plates 242 that are relatively stiff and resist bending to protect piezoelectric material 244 from the bending problem. An alternative piezoelectric sensor 250 (shown in FIG. 9B) includes "I-beam" plates 252 that also protect piezoelectric material 254 from bending. (Plates 242 and 252 are otherwise similar to plates 32 and 34 in FIGS. 1-3.) It is also desirable that the frame be lightweight and configured to resist plate deformation in the directions of expected high force and moment application, but not in other directions where the applied forces and/or moments are low. These are not requirements per se but the piezoelectric sensor should be sufficiently lightweight so that it is readily portable and resists bending, without adding excessive mass. The point is that the design of the frame around the piezoelectric sensor is important to proper piezoelectric sensor function.

Combination of Piezoelectric Sensor with Other Types of Sensors

For monitoring some parameters, non-piezoelectric sensors can be used, since they are typically lower cost than piezoelectric sensors. Examples include accelerometers for measuring acceleration, and piezoresistive, capacitive, or pressure cell sensors for determining the center of pressure on a prosthesis foot.

It would also be useful to develop piezoelectric sensors that can measure bending. Such a sensor would enable a more complete characterization of the kinetic status at the point of measurement (a conventional piezoelectric sensor measures only x-y-z force (or only force components along one or two axes)). However, a piezoelectric sensor for measuring bending that does not suffer crosstalk from other force/moment components is not currently commercially available.

Another parameter of interest is the position of the resultant force in the prosthesis, for example, the location of the center of pressure on the bottom of the foot, thus allowing sagittal bending, frontal bending, and torsional moments to be determined in the case where only one 3-axis sensor is used, as discussed below. Note that in an exemplary data processing strategy where only one 3-axis sensor is used, measurement of resultant force position (or center of pressure) on the bottom of the prosthesis foot is required so as to distinguish Balanced, Forefoot, and Hindfoot data segments; however, as noted below, the direction of the resultant force can instead be used to make these distinctions, and as a result, this additional sensor may not be needed.

As shown in FIG. 10, the resultant force or center of pressure 266 on a prosthesis foot 260 supported by a pylon 262 is determined in a current exemplary embodiment by using at least three pressure sensors 264 (i.e., Force Sensing Resistors (FSRs), which are currently piezoresistive force sensors—not piezoelectric sensors) on the foot. The center of pressure is then calculated from the piezoresistive data. The calculation is somewhat similar to that for the three (or four) piezoelectric sensors disposed between the plates of a prosthesis described above. The intent is to identify $(x_{cp}, z_{cp})$ such that the summation of moments about z is 0, and the summation of moments about x is 0:

$$\sum_{n=1}^{N} A_n \cdot x_n = 0$$

$$\sum_{n=1}^{N} A_n \cdot z_n = 0$$

where n is the pressure sensor and N is the total number of pressure sensors. By using these equations and the locations of the pressure sensors relative to each other, the location of center of pressure 266 ($x_{cp}$, $z_{cp}$) is readily determined.

Another sensor of interest that can be beneficially included on a prosthesis is one that measures the position of the shear force in the prosthesis, for example on the bottom of the foot. Commercial foot shear sensors do not yet exist but they are expected to be available in the near future. Other possible sensors that can be included are a temperature sensor, a humidity sensor, a velocity sensor (e.g., to determine how fast a person is moving), and a sensor for measuring an angle of the prosthesis (e.g., using a gyroscope), and force sensors within the socket, all of which are of clinical relevance.

A force F is a vector having components $F_x$, $F_y$, $F_z$, directed along axes 276, at a location 278 in FIG. 11A, for a prosthesis foot 270 coupled to a heel 272 and a pylon 274. As further shown in FIG. 11B, for a prosthesis foot 280, force F is applied at a distance a from the y-z plane, and a distance b from the x-y plane, proximate a pylon 282. The length of the prosthesis between the piezoelectric sensor and foot is c (note that c is not shown). By knowing the location of the applied force on the bottom of the foot (i.e., a center of pressure 284) determined by using pressure sensors on the bottom of the foot, as in FIG. 10, for example, and by knowing the components of force in the prosthesis measured with the piezoelectric sensor, the bending moments in x-y ($M_z$), y-z ($M_x$), and x-z ($M_y$) can be calculated. This calculation assumes that the location of the shear forces $F_x$ and $F_z$ on the bottom of the foot is coincident with the location of the axial force $F_y$ there, that the lengths a, b, and c do not change much during loading, and that the orientation of the piezoelectric sensor coordinate system with respect to the directions $F_x$, $F_y$, and $F_z$ do not change much. The most significant approximation is the change in length of c, due to bending of the shank and foot. However, this deformation and thus, any change in c can be calculated through lookup tables characterizing the material properties of the shank/foot. This new length is c'. Similar procedures can be used to correct a and b and the orientation of the coordinate system, if greater accuracy is necessary. The moments of the piezoelectric sensor are calculated as:

$$M_x = -F_y * b - F_z * c'$$

$$M_y = F_x * b + F_z * a$$

$$M_z = F_x * c' - F_y * a$$

This analysis for the calculation of bending moments assumes that the magnitudes of $F_x$, $F_y$, and $F_z$ on the bottom of the foot are the same as those measured at the piezoelectric sensor, which for most clinical applications is an acceptable approximation. In certain applications, for example where it is of interest to consider or calculate energy losses within the shank and foot, these assumptions would not be acceptable. However, corrections can be made to accommodate internal energy changes in the foot/shank (integral of force displacement) through the use of lookup tables.

Location of the Piezoelectric Force Sensor

The piezoelectric force sensor can alternatively be disposed at the lower end of the socket, either end of the pylon, or the top or bottom of the foot (or other terminal device, such as a fin, a ball, etc.), in a standard modular prosthesis. FIG. 12 illustrates an exemplary prosthesis 290 with a foot 292, a pylon 294, and a socket 296. One location for the piezoelectric sensors and plate is at the bottom of the socket/top of the pylon, at a location 298. An alternative location for the piezoelectric sensors and plates is at the ankle, i.e., at the bottom of the pylon/top of the foot, at a location 300.

It is contemplated that in the future, the piezoelectric sensor may be disposed inside one (or more) of the prosthetic components, but the design of the component(s) would need to be changed to accomplish that improvement. However, it is very likely that such a change will occur, because prosthesis manufacturers will likely want to include the force sensor as an integral part of their product. The use of a piezoelectric force sensor as a separate unit is only a temporary condition. The location of the piezoelectric force sensor beneath the socket at location 298 is better than location 300 at the ankle in terms of experiencing a lower sagittal plane bending moment during gait, thus potentially resulting in less crosstalk to the sensor. However, empirical assessments have shown that crosstalk is so low, it might not matter. Also, the forces applied to the socket are typically of greatest clinical interest; there is no distortion introduced by components disposed between the socket and sensor. The ankle location for the piezoelectric force sensor is better in terms of lower sensitivity to changes in prosthesis length due to bending on the foot and ankle.

Further Details of Energy Harvesting Power Source for Sensors and Other Components While a battery power supply has initially been used in several exemplary embodiments discussed above, it is contemplated that an energy harvesting method can instead (or additionally) be used to provide electrical power to each sensor and to the other components of the data monitoring system that are mobile with the user of the prosthesis, such that the energy generated during the user's daily activity powers the device and/or is stored in a battery. An energy harvesting device works on the concept of capturing kinetic, thermal, or chemical energy from the user or as a result of the activity of the user of the prosthesis.

As shown in FIG. 13A, an exemplary device 310 captures kinetic energy via the vibration of small rods 314 (which can also be fabricated of piezoelectric materials) attached to a plate 312 that creates a charge or current (detected by a meter 318) when a dynamic force such as a vibration input is applied to a zigzag electrode 316. A graph 320 in FIG. 13B illustrates the output current of such a device in nanoamperes, for periods 322 of applied vibration, relative to periods 324 when no input is being applied. Details of such a device are disclosed in a publication by Dr. Zhang, entitled "EnergyHarvesting.1.8.10," the disclosure of which is specifically hereby incorporated herein by reference, but simply as background information. One could also use piezoelectric materials in a cruder sense, by capturing the voltage change where a force is applied and released from the piezoelectric material.

Other types of energy that can be harvested, such as thermal, can be alternatively employed, since the residual limb gets hot and comprises a thermal source at a higher temperature than the surrounding environment. An example of a usable thermal energy harvesting device is one of the miniature thin film thermal generators available for example, from Micropelt GmbH, in Germany, which generate an electrical current based on the Peltier effect.

It is also possible to employ a chemical gradient as an energy source, taking advantage of chemical changes that take place within the tissues or materials in the socket as a result of mechanical loading while the user engages in daily activity. However, each of these technologies generates only a small amount of electrical charge or power. By applying force to many piezoelectric rods in device 310 it should be possible to provide sufficient energy, if sufficient numbers of the piezoelectric rods are included. Substrate 312 might be provided to cover a relatively large area of the prosthesis, such as a protected surface disposed on the pylon. It is contemplated that any problems in fabricating such devices can readily be overcome to enable any of these types of energy source devices to be produced and used in the present monitoring system.

Further Contemplated Functionalities for the Force Sensors

It is contemplated that future piezoelectric sensors will include additional integral components that provide additional functionalities while contributing to enhanced portability. For example, the piezoelectric sensor can be equipped with an on-board signal conditioner, which might be mounted adjacent to the sensor if it were made sufficiently small, or with an on-board computer to calculate information of relevance that is then stored to a data logger or communicated in real-time to adjustable components in the prosthesis (e.g., to a power ankle, a power knee, or a volume adjustable liner in the prosthesis socket) to actively control those components. The piezoelectric sensor might also include an integral telecommunication system that periodically transmits data to a data storage system, either local (or included in the prosthesis) or at remote site, e.g., over a wireless link and/or over the Internet, as discussed above. For example, for a gait rehabilitation/training application that is described below, the system can be activated upon the amputee patient's entry into the training room or facility. Data can be automatically and directly transferred to a base computer in the facility. The data can be processed quickly to provide the therapist with updated information on the progress of the session. Numerous telecommunication devices exist, including smart cell phones, and personal data assistants. Numerous wireless strategies are also available to implement this approach.

It is also contemplated that the piezoelectric sensor and other components of the data collection system can enter an energy-saving mode (low power use) during periods of minimal activity, such as when the user is asleep at night and the prosthesis is not in use or while the user is simply sitting still. This approach is comparable to that used on laptops for reduced power consumption at times when the laptop processing capability is not being used.

Data Processing Strategy

An exemplary embodiment employs a data processing strategy whereby all of the collected data are segmented into groups based on the force and moment data that have been collected. These groups serve as the base segmentation for additional analysis, as described below. Details 330 of such a strategy are illustrated in FIGS. 14 and 15, and discussed below. It must be emphasized that the processing strategy and applications of the results produced by that strategy are also equally applicable to data produced by other types of sensors beside piezoelectric sensors. It is contemplated that for many applications, the high frequency response and/or range of the piezoelectric sensors may not be so important, so that other types of sensors can be used to produce the data that are processed in accord with the strategy described below. Furthermore, new types of sensors may have characteristics equal or exceeding those of the piezoelectric sensors discussed herein, so that the following processing strategy will thus be equally usable with the data produced by such sensors.

The output from the piezoelectric force sensor (i.e., $V_x$, $V_y$, $V_z$) in a block 332 are corrected for offset (drift) and converted to forces using calibration data in a block 334 to determine a new result defined as forces $F_x'$, $F_y'$, and $F_z'$. Because the discharge rate of the sensors is very slow, the drift is slow and is easily identified as a very low frequency component in the sensor data. The drift is accommodated by determining its value and subtracting it out from the sensor channels. These forces and the distance from the piezoelectric sensor to the bottom of the prosthesis foot in a block 338 are used with the location of the center of pressure in a block 340 in a block 336 in connection with a lookup table to determine load deformation on the foot/ankle shank system of the prosthesis to correct the $y_{cp}$ if needed, producing new results, $y_{cp}'$, and similar steps are used to determine corrected values, $x_{cp}'$ and $z_{cp}'$. In a block 342, calibration data are used to correct for any crosstalk, if needed, and convert to $F_x$, $F_y$, $F_z$. The results are then used to calculate three moments in a block 344. In a block 346, the forces and moments are input to the processing strategy for analysis, as discussed below.

One purpose of the data processing strategy is to prepare a set of continuous data collected for a patient for interpretation by a medical practitioner. This analysis can be conducted in real-time as the patient engages in their daily activity, either using a processor disposed on-board the prosthesis or remote from the patient, or it can be conducted after downloading collected data, for example via the WiFi or Bluetooth telecommunication system described above. To carry out the processing methodology, the time periods during which the kinetic monitoring system entered sleep mode are identified and time-stamped. The remaining data streams are broken up into segments of equal time intervals. The duration of the time interval is selected to match the features of interest for the analysis at hand. Because walking is typically a strong feature of interest, the time interval can be set, for example, to be approximately equal to the duration of at least two walking steps, so as to ensure that at least one complete walking cycle is captured within each segment. However, it must be emphasized that time intervals of other duration can also be used with the present approach and it is not intended that this concept be limited to the two walking step example noted above. Each segment is time-stamped so that later, the time it occurred and its time position relative to other segments can be identified.

The idea of dividing the data into equal segments from the outset and then grouping them for subsequent inspection, which is described above, is a key concept in this processing scheme. It enables the subsequent clinical applications to be executed with ease. Further, it allows all data to be included in analysis. In the past, most researchers have started with a different strategy, trying to recognize patterns in the data as corresponding to certain activities, and then eliminating or not further considering data that were not recognized.

FIG. 15 is a block diagram 350 illustrating exemplary details showing how the data can be analyzed. To conduct the first phase of the analysis in a step 353, processed force sensor data 352 ($F_x$, $F_y$, $F_z$, $M_x$, $M_y$, $M_z$, $X_{cp}$, $Y_{cp}$, $Z_{cp}$, in this example) are divided into data segments of equal time intervals and time stamped. The resulting segments are then separated into a static group 354 and a not static group 356, and each segment is analyzed to assess a change in force and moment within the time segment. The differences between the maximum and minimum force and maximum and minimum moment are calculated. If the difference is more than a selected percentage of the applied force or moment (typically about 10-15%) then the segment is classified as "static." If the difference is greater than the selected percentage, then the segment is classified as "not static."

Static:

The segments identified as static are then grouped according to the position of the applied force on the bottom of the foot during each segment, which can be determined using the data from either a bending piezoelectric sensor, another bending sensor, the center of pressure sensor(s), from a resultant force position sensing sensor, or from the piezoelectric sensor data—assuming three (or four) 3-axis piezoelectric sensors are used. Alternatively, a configuration of a single 3-axis piezoelectric sensor, as well as three or four separate piezoresistive, capacitive, or pressure cell sensors can be used instead. Rather than using the position of the applied force, the orientation of the resultant force vector can be used instead of its position, in which case, only the x-y-z components from the piezoelectric sensor are needed. In the description that follows, the position of the center of pressure is used.

The segments are characterized as balanced loading (BA) 358, heavy forefoot loading (FF) 360, or heavy hindfoot loading (HF) 362. The following approach is used for this characterization. If the position of the force is anterior to the arch of the foot, then a characterization of "forefoot" is assigned. If it is posterior to the arch of the foot, then "hindfoot" is assigned. If it is in the region of the arch, then "balanced" is assigned. Alternatively, the orientation of the applied force can be used to characterize forefoot, hindfoot, and balanced.

In this exemplary approach, the data are divided based on sagittal plane configurations (e.g., hindfoot, forefoot). However, if frontal plane information were of interest, then medial and lateral positions could be used instead. The choice depends on the analysis of interest.

Each group (Static-Balanced, Static-Forefoot, Static-Hindfoot) is then characterized as to the magnitude of applied force. The three characterizations (low 368, medium 370, and high 372) are specified relative to the patient's body weight. Exemplary specifications are as follows: "high" is above 70% body weight; "medium" is between 30% and 70% body weight; and, "low" is less than 30% body weight. These specifications are adjusted according to the analysis of interest. Thus, using the above-described methods, there are a total of nine possible characterizations of static data segments, or nine possible "activities."

From this classification strategy, quantitative analysis of the activities is conducted to extract information of clinical interest, as described below. These include, for example, the total time spent doing the activity within the measurement period (the measurement period is typically one day, one week, one month, or more than one month) or the change over the course of the measurement period. The duration of activity, magnitude of applied force or moment in terms of mean, median, standard deviation, and other such calculations can be performed to more completely characterize the period of activity, the time of day it was conducted, and other features. The clinical applications of these strategies are described in more detail below.

Not Static:

For not static data 356, the segments are characterized as either cyclic 364 or isolated events 366. "Cyclic" is defined as a segment that contains a cycle, at least a portion of which is repeated. For example, the stance phase is a repeated part of consecutive steps of walking; the force returns to 0 during this phase. Repeatability within a segment is investigated using well-known pattern recognition strategies described in detail in the scientific literature. Strategies include target recognition, principal component analysis, iterative closest points, dynamic time warping, and other strategies to identify characteristic waveforms of interest. "Isolated events" are those that are not deemed cyclic and are thus characterized by the non-cyclic nature of the data within the segment. Examples include rising out of a car, jumping off a ledge, or some other dynamic activity that is singular in nature.

The cyclic data segments are then grouped into balanced, forefoot, and hindfoot groups, based on the location on the bottom of the foot where the applied force is directed, as discussed above in connection with static data 354. Segments for which the force is applied mainly in the forefoot are labeled as "forefoot." Segments for which the force is applied mainly in the hindfoot are labeled as "hindfoot," segments for which the force is applied part of the time in the forefoot and part of the time in the hindfoot, or are applied only to the arch region of the foot, are labeled as "balanced." For example, walking up stairs would be expected to generate forefoot loading, while walking on a flat surface would be expected to generate balanced loading. Alternatively, the characterizations forefoot, hindfoot, and balanced are used to characterize the orientation of applied force within the segment. The isolated event segments are also grouped according to the location or orientation of applied force, using a strategy similar to that described above for the cyclic data segments.

Each of the three groups (Cyclic-Balanced, Cyclic-Forefoot, Cyclic-Hindfoot) is then divided into three subgroups based on the magnitude of applied force, using the maximum, mean, or median within the segment or another calculation from the data. The three characterizations (low, medium, high) are specified relative to the patient's body weight. Exemplary specifications are: "high" is above 130% body weight; "medium" is between 70% and 130% body weight; and, "low" is less than 70% body weight. The percentiles for not-static loading, in general, are higher than those for static loading because the dynamic activity induces greater forces. Applied forces during walking, for example, are often 1.2 to 1.5 times a patient's body weight. These specifications are adjusted according to the analysis of interest (described in more detail below). Similarly, each of the three groups (IsolatedEvents-Balanced, IsolatedEvents-Forefoot, IsolatedEvents-Hindfoot) is divided into three subgroups based on the magnitude of the applied force, using methods similar to that employed for cyclic segments, as described above. Thus, using the above-described methods, there are a total of 18 possible characterizations of not static activities. Further subdivisions of activity are possible. For example, the Cyclic-Balanced-MediumForce activity can be further subdivided by dividing the repeated cycle segments into multiple sections and employing an artificial intelligence based system to assess alignment, similar to efforts pursued in the 1990's.

Each of the 18 characterizations, in addition to the nine static ones described above, represents a collection of biomechanical events. While each characterization does not necessarily represent only one action, they are "action-like." For example, for the Cyclic-Balanced-MediumForce case, segments with high amplitude force early in stance phase that are of much greater magnitude than those later in the stance phase suggest an uphill-like or stair-climbing-like action. While it is not possible to definitively say that the patient was climbing stairs when these data were generated, it is possible to conclude that the action was "climbing-stair-like." For the clinical practitioner, this characterization provides good insight, providing a base for query of the patient for further details of the actual activity in which the patient was involved, if needed. It is important to understand that it is the biomechanical characterization that is of clinical utility.

Presentation of a Summary to the Physician or Practitioner

The data presentation extends from a chart, such as the exemplary chart shown in FIG. 15. This Figure illustrates the base layer (base data presentation), and from it, a more detailed presentation is possible depending on the clinical application and desired insight of the user, as described in greater detail below.

FIG. 16 illustrates a flowchart 380 illustrating exemplary logical steps that may be carried out to prepare a practitioner report based upon the characterizations determined from the analysis of FIG. 15. In a step 382, a body weight for the patient is input, and in a step 384, the analysis resulting from FIG. 15, which is referred to here as "the kinetic record," is input. In a step 386, the kinetic record data are normalized to the body weight of the patient that was input in step 382. In a step 388, the loading sequences that are cyclic and balanced, as noted above in the description of FIG. 15, are isolated from the data included in the normalized kinetic record for the patient, resulting in a subset of the data from FIG. 15. The software program then compares the isolated loading sequences or segments to gait patterns of interest, for example, stair step kinetic pattern(s) input in a step 390 and incline step kinetic patterns input in a step 392, to compute pattern frequency in a step 394. Stair step and incline step kinetic patterns are considered exemplary. Patterns for other activities could be used in addition to these, or instead of these, for example, jumping, transfers, stooping, maneuvers (e.g., turning), donning, and doffing. It is envisioned that as knowledge and understanding of real-world gait activity enhances, other kinetic patterns will be added. A step 396 computes a cadence range for the patient when walking or engaged in other activities, and a step 398 computes event frequency. The results of steps 394, 396, and 398 are then used to create a practitioner report in a step 400.

An exemplary practitioner report might indicate that a patient wore a prosthesis for 70 hours over about a 7 day period (i.e., about 156 hours total time). The report might also show that the patient conducted stair-climbing-like activity for 20 minutes each morning and incline-climbing-like activity for 15 minutes each afternoon. The report might also show that the most of the time while wearing the prosthesis, the patient experienced either balanced weight bearing or forefoot weight-bearing of low to moderate intensity, suggesting that the patient engaged in activities where the patient stood stationary and weight shifted, for example, while working at a bench or counter.

The value of this presentation strategy to the practitioner is a complete picture of the data collected during the monitoring period within a single view. For example, using a timeline series of blocks or a collection of blocks, where each block indicates the type of activity conducted and its duration. The practitioner report or presentation will thus enable the physician or practitioner to gain insight into what the patient was truly doing and how often the patient engaged in specific type(s) of activity. With experience, the practitioner will quickly grasp information from this presentation and will learn where to investigate in more detail.

For example, an exemplary bar graph 470 in FIG. 22 shows the magnitudes of forces experienced by the prosthesis over a three-day period (as a function of the fill used for each bar). In this graph, solid bars 472 indicate that activities involving high magnitude forces occur at about the same time each day and are of relatively consistent duration. The practitioner may inquire and determine that the high magnitude force is likely the result of the patient having to descend several flights of stairs to reach a job location in a building, each day. For example, without being provided the force data, the patient might not have thought to make note of this activity to the practitioner.

Clinical Applications
Use of the Device for Gait Training and/or Rehabilitation

Following an amputation, individuals are commonly provided with physical/occupational therapy and training in order to develop the functional skills required for ambulation (lower limb) or manipulation (upper limb). Such skills may include balance training and partial weight bearing on a new prosthesis. The therapist/prosthetist typically relies upon visual inspection and patient feedback to monitor this process and provides verbal suggestions for activities that enhance rehabilitation. Including the kinetic monitor in treatment provides a means for the therapist to directly monitor the progression of the patient's balance and weight bearing so as to prescribe the optimal rehabilitation program and adjust it accordingly.

The data processing strategy described above is extended to provide clinically relevant information to the patient and healthcare team for the purposes of developing and monitoring rehabilitation programs. For example, a physical therapist working with an amputee patient may develop a rehabilitation plan that is intended to slowly increase weight bearing on the residual limb following amputation. Too much weight bearing too soon can jeopardize the residual limb and prolong recovery. However, partial weight bearing is beneficial as it accommodates the limb soft tissues to the prosthetic socket forces and stimulates healing. In such cases, it is common for the patient to be provided with a walker or a cane along with the prosthesis so as to allow this transition. However, the process of partial load bearing is very subjective and must be monitored carefully by multiple visits with the therapist. Here, the kinetic monitoring system discussed herein can serve as a means to carefully monitor the rehabilitation process, individualize goals for the patient based upon their recovery, and document the efficacy of the interventions (both therapeutic and prosthetic).

In this example, the therapist would use the kinetic sensor data processing software, which implements the logical steps discussed above, to select one or more specific parameters of interest (e.g., axial force) and set loading goals for the patient. Initially, the therapist might select 25% of body weight for up to one hour per day as the target goal for week one. The therapist can then customize the software interface (i.e., a Patient Activity Summary) so that only selected data and/or charts are presented to the patient on their own computer, cell phone, or other communication device. In the Patient Activity Summary shown in a graph 410 in FIG. 17, information is limited to axial forces generated during cyclic loading (i.e., periods of ambulation) so as to enable the patient to see if they have used their prosthesis in excess of the recommended time, i.e., if the loading on the prosthesis is over a target zone 412 (dotted background area), or under the target zone.

Between patient visits with the therapist, the patient can work to meet the interim goals and monitor his or her daily progress. This data can also be sent remotely to the therapist so that progress can be monitored without the need for a patient visit. The therapist can use the available prosthesis sensor data to revise the treatment plan based upon the patient's progress, which creates a dynamic, individualized, evidence-based approach to explicitly address each patient's needs.

In the above example, the therapist might elect to use the more advanced features of the kinetic monitor data and the software that processes it to create customized reports to assess use and activity patterns of the patient before the patient returns to the clinic. Since the therapist is interested in documenting the patient's progress, the therapist can select the Static Activity Summary shown in FIG. 15, to provide information from the three static groups (balanced, forefoot, and hindfoot) at all three load levels (the nine left boxes in the lower row under static data for the Figure). In FIG. 17, the load levels are illustrated in more detail, showing how progress occurs over time and the relative percentage of low loading is more evenly distributed over a 7-day course of therapy designed to increase weight bearing.

FIG. 18 is a graph 420 showing a summary of static activity for a specific patient XYZ. The Figure shows the patient's weight-bearing progression over 11 weeks of treatment. In this example, the therapist instructs the patient to use the prosthesis several hours a day, initially. As healing progresses, the patient is asked to wear the prosthesis more and slowly put more and more weight on the prosthesis. After seven weeks, the patient's total daily duration of weight bearing plateaus, but the durations of medium and high weight bearing have steadily increased, while low weight bearing has decreased. The magnitude of weight bearing increases from week 8 to week 11, although the total duration of all weight bearing levels stays relatively constant. Based on the data presented in FIG. 18, the therapist would be encouraged that the patient is adapting to the use of the prosthesis, and the frequency of therapy sessions might be reduced. The patient is ready to transition to a new level, and prescription should be advanced to the next step.

As another example, the left side of FIG. 19 shows a representation of a prosthesis foot 430 with a pylon 432 of a patient that presents with standing instability and excessive postural sway during equal weight-bearing. Postural sway is presented by selecting the "current" tab, thereby cumulatively graphically displaying the real-time loading magnitude and position of the loading 434 on the bottom of the foot, as well as other visual real-time information. The type of line (i.e., solid, dotted, or dash) reflects magnitude (which might better be indicated by the color of the line), and the position of the line reflects the location of the resultant force on the bottom of the foot.

The excessive postural sway is a sign that this patient is unstable and not yet ready to proceed to ambulation without use of an assistive device. The therapist elects to have the patient train with a walker so as to provide extra security and safety to the patient. Later, the therapist can again assess postural sway to determine if and when the patient is ready to begin independent ambulation activities. For example on the right side of FIG. 19, at a time five days after the data shown on the left side of the Figure were collected, it is apparent that the recommended training has resulted in a much reduced real-time loading magnitude of the swaying 436.

The kinetic sensor system described herein can further be used during this time to provide warning to the user that at-risk activities are being conducted, for example, an excessive heel moment is being applied during ambulation that puts anterior distal soft tissues on the residual limb at risk. Or, a high shear force is generated during walking, indicating that the patient is applying a high braking force in early stance and thus, inducing an energy inefficient gait. Real-time analysis of the kinetic data provides a means for the system to alert the user to potential problems through audible or vibratory warnings. This encourages the user to adapt their walking pattern and avoid the adverse event. Further, through more detailed presentation of the Cyclic Activity Segment data and the presentation of data from many steps or presenting an average step, the practitioner is able to identify poor gait patterns and make the adjustments needed to the prosthesis components. For example, adjustments to the prosthesis length, alignment, or suspension might be deemed necessary.

For the physician that prescribes a prosthesis or other related treatment for an individual with limb loss, the kinetic data are potentially of strong clinical value because physicians are typically not present in therapy sessions. The kinetic records may be saved and stored for reference by the physician or other members of the clinical team. The kinetic monitor data supplements feedback from the therapist and patient, providing quantitative insight into the patient's status. The physician is thus able to make a more informed decision for future prescription and treatment than is achieved using current clinical techniques.

Later in the rehabilitation process, the kinetic monitor data can be used to reinforce positive outcomes, enabling the patient to take an active role in their own rehabilitation or training and improve the speed and quality of the outcome. The data processing strategy described above facilitates this presentation because of the way in which the data are grouped. For example, to determine the lengths of activity periods, e.g., during cyclic activities, the segment data within a category, such as cyclic, are inspected to determine the number of sequential segments. The number of sequential segments is proportional to the duration of the activity period.
Use the Device to Identify Over/Underuse Injury and Imminent Injury Individuals with limb amputation are prone to a number of medical conditions, such as elevated back pain, joint pain, osteoarthritis, osteoporosis, and osteopenia that may be caused by asymmetrical or abnormal loading of the limbs. The kinetic monitor disclosed herein provides a means to better study these conditions as well as facilitating interventions to address them. The high sensitivity and wide frequency range provided by the piezoelectric sensors are far superior to other technologies for this purpose.
Instability For example, when a person with limb amputation using a prosthesis experiences a volume reduction in the residual limb or if the person wears a socket that is loose on the residual limb, "pistoning" occurs. Pistoning is the result of slip between the limb and socket. While the foot is on the ground the residual limb goes deep into the socket, load is transferred from the prosthesis through the residual limb to the bony skeleton to support weight bearing. However, as the patient lifts the prosthesis off the ground as is done during the swing phase of gait, the residual limb pulls out of the socket. Some pistoning is good for some patients because it releases occluded blood flow within the limb, facilitating reperfusion. However, too much pistoning causes the connection between the residual limb and socket to become unstable, putting the person using the prosthesis at risk of injury and falling. Further, slip between the residual limb and socket can induce frictional stresses on residual limb skin, which are threatening to residual limb tissue health. Frictional stresses are stresses tangential to the skin accompanied by sliding (slip) between the skin and loading surface. Research has shown that skin is more prone to injury if there are frictional stresses between the skin and supporting surface than if there is shear stress (no slip). Thus, it is desirable to avoid slip, while at the same time not overstressing limb soft tissues to the point that blood flow is occluded. It is therefore desirable to identify the presence and degree of unstable coupling between the limb and socket so that changes can be made to the prosthesis, either directly through communication from the sensor output to a controller for an active component (e.g., an adjustable socket size device like a fluid-filled insert, electro-active polymer liner, or a vacuum assist unit) to reduce or compensate for the slip, or manually.

Unstable coupling can be caused by other sources as well. For example, if a patient uses a liner that is too soft, components that are not well matched to the patient, or if the patient does not have good proprioception, then unstable coupling between the residual limb and prosthesis can occur. Again, it is desirable to detect the presence and degree of unstable coupling so that changes can be made to the prosthesis or treatment to reduce or compensate for it.

Through analysis of cyclic data from the present kinematic force monitoring instrument, it has been shown using data collected on amputee subjects that when there is unstable coupling between the residual limb and socket (in this case induced by removing the locking pin from the amputee subject's liner), a detectable perturbation 444 is apparent in the data (see the exploded view of the data in a circle 442 in a graph 440 shown in FIG. 20A) soon after heel contact. Note that this perturbation is not apparent when a strain-gage force sensor is used (see corresponding portion 452 of a graph 450 shown in FIG. 20B). The reason the piezoelectric sensor used in all of the exemplary embodiments discussed herein detects these changes while other sensors do not is that this piezoelectric sensor measures dynamic force—while other types of sensors, such as strain gages, piezoresistive, capacitive sensors or pressure cells, lack its sensitivity and/or frequency response for such measurements. The ability of the piezoelectric sensor to measures dynamic forces with a high sensitivity over a wide range of frequencies makes it an ideal sensor for detecting problems and issues such as slippage caused by the unstable coupling between a patient's residual limb and the socket of the prosthesis being used by the patient. In contrast, other types of force sensing instruments do not record with such high sensitivity over such a wide frequency range, and thus, are not capable of picking up this information. However, it is contemplated that new designs for piezocrystal or piezoceramic force sensors may be developed that equal or exceed the capabilities of the piezoelectric sensors discussed herein. Accordingly, as used herein and in the claims that follow, the term "piezoelectric sensor" is intended to broadly encompass any type of force sensor that includes a piezoceramic or piezocrystal material and has the ability to sense dynamic forces over wide ranges and with high frequency sensitivity. The frequency range of the PCB Piezotronics sensor used in an exemplary embodiment is 0.001 Hz up to 5-10 kHz, the resolution is 0.006 lb-rms, and the non-linearity is less than 1% full-scale at a sensitivity of 5 mV/lb. What is relevant is the fact that across at least the range of 0.001 Hz to 30 Hz, the sensitivity is high, noise is low and uniform, and also phase linear. The reason that a 30 Hz maximum is noted is because most gait analysis events occur within this range. For most clinical applications discussed in this application, this bandwidth is all that is of interest. However, for certain applications, such as high impact events or possibly limb-socket coupling issues, a range 0.001 Hz to 100 Hz is more appropriate. It is not clear what maximum frequency might be appropriate to specify, but frequency content above 500 Hz seems unlikely. Since force plates typically sample at 1000 Hz, based on the Nyquist theorem, it seems appropriate to specify 500 Hz at the upper limit.

Further, it should be understood that this measurement of dynamic force is different from a measurement of acceleration. Acceleration is a measurement of the displacement over time of a mass subjected to a perturbation force, i.e., a=F/m. A number of researchers have used accelerometers in gait analysis in an effort to identify signature patterns indicative of instability. However, such efforts have not proven successful, because currently available accelerometers apparently do not provide a true indication of dynamic force with range and frequency response of a piezoelectric sensor.

Perturbations, like the example shown in the Figure, are identified in processing through analysis of the cyclic segment data or isolated event data. As noted above, cyclic segments are processed to identify walking-like actions and other specific actions, such as climbing-like actions. These actions are identified by extracting data where the force returns to a baseline (e.g., zero) at least twice within the segment, and the duration of the baseline value period is beyond a threshold value. Then, the loading portion of stance phase of each segment is extracted, and a spectral analysis of that portion conducted. For the example shown in graph 440 in FIG. 20A, the frequency of perturbation 444 (in circle 442) is about 33 Hz. Spectral analysis results show a peak outside the bandwidth of normal walking that identify the perturbation. Alternative strategies are to search the post-heel contact portion of cyclic activity segments for oscillations, to use pattern recognition methods to match the cyclic activity segments to normal and abnormal model waveforms, and then to use artificial intelligence or other computing methods to relate selected features of the data for identifying the actions.

Once a perturbation related to an action is identified, this knowledge can be used to improve clinical treatment. For example, the information derived from this analysis can be communicated to the patient and/or to the practitioner via data transmission. Adjustments to the sleeve, strap, suspension, and/or other components of the patient's prosthesis can be made. Alternatively, the data can be transmitted to components on the prosthesis that are capable of adjusting the socket shape/volume or suspension system, for example, to an automatic vacuum control system, a fluid-filled insert, or a related automated adjustment system provided to modify some fit parameter of the prosthesis.

Waveform Analysis

The software instructions that are implemented by a computing device used to process the dynamic force and other parameters monitored by the exemplary embodiment can enable a practitioner to examine independent features of a cyclic waveform. Waveforms may be examined either independently (i.e., as a single step), as a collection of waveforms, or as averaged waveforms. Once selected, the software analysis features enable the practitioner to visualize and measure key features of gait, such as loading/unloading rate, maximum/minimum force, and/or peak timing. In the example shown in a graph 460 in FIG. 21, the axial force, $F_z$ applied through the prosthetic pylon is being visualized to assess the vertical loading and unloading rates ($\Delta_{z1}$ and $\Delta_{z2}$), peak loading response force ($F_{z1}$), minimum midstance force ($F_{z3}$), and peak propulsive force ($F_{z2}$), as well as the timing of those events ($t_{z1}$, $t_{z3}$, $t_{z2}$) (see the example shown in FIG. 22).

The data processing strategy described above facilitates practitioner efforts to identify biomechanical sources of a patient's difficulties and thus, to improve clinical care. For example, consider a case where the patient presents with irritated anterior distal residual limb tissues. The base data presentation chart shows high load application during isolated events-forefoot segments only. By presenting to the practitioner how often these events occur and when they occur, the practitioner and patient gain insight into the source of the at-risk behavior. The timing of the events is easily calculated from the base data presentation format by identifying the timing of the isolated events segments of high magnitude from the time-stamp data, and presenting the information on a timeline of the monitoring period. A series of isolated events-forefoot each morning would indicate that the events are part of a daily morning routine (e.g., as in FIG. 22), and thus careful inspection of that period should be made.

The analysis of the data collected by the kinetic monitoring system discussed above can apply pattern recognition strategies, including target recognition, principal component analysis, iterative closest points, dynamic time warping, and other strategies to identify characteristic waveforms of interest, or to group collected segments based on similarities in their shapes. The strategy for pattern recognition can be incorporated into an on-board computer included in the kinetic monitoring system on the prosthesis (or otherwise portably carried by the user of the prosthesis), and an alert can be provided when the patient conducts a potentially hazardous activity. This effort represents an advance over the use of just a magnitude threshold to warn a patient of an at-risk activity, because it is more specific and is tailored to the patient's individual characteristics. Alternatively, when an at-risk pattern is recognized, signals can be sent to on-board components to enable automatic adjustment of components on the prosthesis to reduce the risk of falling, for example, by adjusting the stiffness of the prosthetic liner, or the position of the prosthesis foot relative to the pylon/socket.

As insight into the clinical relevance of different isolated event waveforms emerges through use of the dynamic piezoelectric force sensor on amputee patients, processing algorithms and pattern recognition strategies will also be enhanced. New subcategories will likely be created. In other words, the blocks in the base data presentation, particularly the isolated event blocks, are likely to be sub-grouped further, based on the clinical meaning and need. In a similar manner early stumble-like or fall-like behavior can be identified and categorized. These efforts will help detect fall-like behavior so that interventions can automatically be made before an injury occurs, where the intervention can include both automatic adjustments to the prosthesis and automatically contacting the practitioner.

Overuse/Underuse

Overuse or underuse of a prosthesis by a patient is investigated initially at the level of durations of different activity blocks in the base data presentation prepared using the kinetic monitoring system. The frequency of occurrence of different activities and when they occur allow quantitative characterization not only of activity but of the types of activities the patient is conducting. Further analysis enables more detailed characterization. For example, through analysis of the averaged, long-term cyclic data, researchers and medical professionals can examine the relationships between the incidence of overuse medical conditions and key features in the kinetic record. Spectral analysis may reveal damaging frequencies in the kinetic signal that are delivered to the residual limb, or analysis of net impulse or signal power may indicate excessive overall energy delivery to the limb. Through spectral analysis of the signal content for different segment groups, as well as force-time integral calculations to assess energy delivery, and other analyses, the overuse or underuse of the prosthesis is well determined. These long-term analyses may reveal associations between ambulatory activities and long-term medical conditions. This information can then be used to determine the need for, and effect of preventative interventions by the medical practitioner.

Use of the Device to Select or Change Component Prescription (Shank, Foot, Powered Device, Limb Length, Volume Control)

The selection of prosthetic components (i.e., feet, pylons, knees, etc.) is determined by the managing healthcare team that includes a physician and a prosthetist. Prosthetic components are currently commonly selected based upon the patient's reported activity level and types of activities that the patient chooses (or is able) to perform. Little objective evidence is used to substantiate statements made by patients about their normal daily activities or evaluate when patients require the use of different components. The inclusion of the kinetic monitoring system discussed above with a prosthesis offers a means for the practitioners to visualize and objectively quantify the activities actually performed and based on the objective data, recommend optimal components that match an individual patient's needs. It is expected that the reimbursement (i.e., by medical insurance) for specialized prosthetic components will require such evidence in the future. The software algorithms employed to process the force data and other monitored parameters provided by the present kinetic monitoring system can be used to derive individualized patient reports that document the frequency of patterns resembling key activities, such as stair-like ascent/descent and isolated events, as well as quantifying the range of cadence over which the patient ambulates. Since these parameters are the criteria upon which selection of and reimbursement by insurance for prosthetic components is based, this report is invaluable to the practitioner and aids in the clinical decision-making process.

For example, the detailed activity and type of activity data provided from the kinetic piezoelectric force sensor enables activity characterization in greater detail than the traditional MFCLs (Medicare Function Classification Levels) traditionally used. Thus, rather than using a qualitative description of household ambulator, prosthesis use can be characterized based on the information presented in the base data presentation produced by the kinetic monitoring system. In other words, threshold durations for different biomechanical groups (blocks) can be used for classification. The quantitative information facilitates matching the appropriate components to the patient, and further, facilitates a needed change of the prosthesis components as the patient's capabilities change.

New prosthetic feet are characterized based on what they should accomplish, in terms of function. A foot on a prosthesis provided to a patient might be configured to more effectively facilitate healthier toe loads, for example. The data provided by the piezoelectric force sensor used in the kinetic monitoring system facilitates matching the patient to the components via the biomechanical characterizations and other categorizations the kinetic monitoring system provides. For example, if a patient engages in activities that have much forefoot loading, a healthy toe foot configuration should be prescribed. The algorithms should recommend treatment for individual cases, for example, indicating that powered components should be used for a patient based on the data collected by the kinetic monitoring system. Once the kinetic monitoring system is used extensively on patients, and patterns of performance are recognized, this new approach will become even more capable of correctly predicting appropriate components for the prosthesis used by a patient.

In addition to recommending components for the patient based on the monitored data, the kinetic monitoring system data will be used to evaluate the effects of a component change once it is made, potentially providing justification for the medical costs to payers (e.g., insurance companies) of the expenses incurred in this process.

Use the Data to Select or Change Socket Style Prescription

The data collected with the kinetic monitoring system represent boundary conditions for analytical models that facilitate liner selection for individual patients. The selection of an appropriate liner is important to a patient's residual limb health and limb-socket stability, because it affects force transfer from the prosthetic socket to the residual limb. The selection of a liner is based, in part, on the activities the patient conducts and the gait style.

A computational finite element liner/limb model can employ the data collected by the kinetic monitoring system to predict loading conditions on the residual limb as well as features related to tissue health that are derived from that analysis, including internal energy changes within limb tissues, skin tensile loads, shear loads, and frictional loads. The liner/limb model thus serves to identify the relationship between the piezoelectric force sensor data collected by the kinetic monitoring system and tissue response and stability, and to optimize liner selection so as to achieve an acceptable tissue response with appropriate stability. The model also serves as a means for using insight into the effects of pistoning detected with the kinetic monitoring system (as described above) and how adjustments to the socket shape and volume affect limb tissue health. An example of the use of this model to show stresses that are normal to the surface of a residual limb when fitted into a prosthesis socket is illustrated in a graph 480 in FIG. 23. The gray scale shows the magnitude of the normal forces experienced by the patient's tissue, where the darker the grayscale (such as in a region 482), the greater the force is.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for collecting, processing, and employing data indicative of kinetic parameters experienced by a prosthesis while a user fitted with the prosthesis engages in activities, comprising the steps of:
    (a) attaching one or more pre-loaded piezoelectric sensors to the prosthesis to monitor forces experienced by the prosthesis as a result of the user wearing the prosthesis while engaging in the activities, each of the one or more pre-loaded piezoelectric sensor developing a charge indicative of a kinetic parameter experienced by prosthesis;
    (b) amplifying the charge produced by each of the one or more pre-loaded piezoelectric sensors, producing a corresponding output signal indicative of the parameter experienced by the prosthesis, the output signal from each of the one or more pre-loaded piezoelectric sensors being used to produce the data indicating the kinetic parameters; and
    (c) processing the data to determine the kinetic parameters experienced by the prosthesis and for evaluating conditions related to use of the prosthesis by the user, wherein the step of processing the data includes the steps of:
        (i) segmenting the data into equal duration data segments by dividing the data by a predetermined interval of time, wherein a duration of the predetermined interval of time is selected to match features of interest needed to carry out a desired analysis of the data;
        (ii) determining an applied force or moment for each of the data segments over the duration of the data segment;
        (iii) characterizing each of the data segments into groups based on a difference between a maximum and a minimum of the applied force or moment of the data segment in comparison to the applied force or moment measured by the one or more pre-loaded piezoelectric sensors.

2. The method of claim 1, wherein the step of processing comprises the step of characterizing the activities that are carried out by the user while wearing the prosthesis.

3. The method of claim 1, wherein the data comprise two or more parameters selected from a group of parameters consisting of:
    (a) a component of force directed along one of a plurality of orthogonal axes;
    (b) a moment relative to at least one of the plurality of orthogonal axes;
    (c) an indication of the prosthesis bending;
    (d) an indication of at least one parameter on a foot portion of the prosthesis, where said at least one parameter is selected from a group of parameters consisting of:
        (i) a resultant force position;
        (ii) a direction that a force is applied; and
        (iii) a center of pressure;
    (e) an indication of a position where a shear force is applied to the prosthesis;
    (f) a temperature of a portion of the prosthesis;
    (g) a velocity of the prosthesis as the user moves about;
    (h) an angle of the prosthesis; and
    (i) a force inside a socket of the prosthesis.

4. The method of claim 1, further comprising the step of supplying electrical energy to energize the one or more piezoelectric force sensor and other components used for collecting the data by harvesting energy as a result of the activities in which the user engages while wearing the prosthesis.

5. The method of claim 4, wherein the step of supplying electrical energy comprises at least one step selected from the group of steps consisting of:
    (a) using a force resulting from the user engaging in activity to provide an input to a piezoelectric generator, producing an electrical output current;
    (b) using a temperature differential developed between a portion of a body of the user and an environment to generate the electrical output with a Peltier device; and
    (c) using a chemical gradient developed due to a chemical change that occurs as a result of the activity of the user within one of a tissue of the body of the user, and a material of the prosthesis.

6. The method of claim 1, further comprising the steps of:
    (a) communicating the data to an automatically adjustable component of the prosthesis; and,
    (b) using the data for automatically adjusting the component to more effectively fit the prosthesis to the user, in regard to the activity of the user.

7. The method of claim 1, further comprising the steps of:
    (a) automatically activating collection of the data when the user is at a specific predefined location where the user engages in a training session; and
    (b) processing the data that were automatically collected to provide at least one of a medical practitioner and the user with information about a progress of the user in the training session.

8. The method of claim 1, wherein the step of processing the data includes the steps of preparing and presenting a report showing information derived from the data, to provide feedback to the user about a condition related to the use of the prosthesis by the user, wherein the information comprising the report are presented to the user on a device that is readily accessible by the user.

9. The method of claim 1, wherein the step of processing the data includes the steps of automatically:
(a) identifying a pattern for an activity being performed by the user;
(b) detecting whether the activity places the user at risk of injury, and if so, carrying out at least one of the steps of:
(i) warning the user that the activity identified is placing the user at risk of injury; and
(ii) automatically adjusting a component of the prosthesis to reduce a risk of injury to the user as a result of the activity recognized.

10. The method of claim 1, wherein the step of processing the data includes the step of processing the data to provide information for enabling a medical practitioner to determine if the user is either overusing or underusing the prosthesis, or is at a risk of an injury, when engaging in one or more activities.

11. The method of claim 1, wherein the step of processing the data includes the step of processing the data to provide information for enabling a medical practitioner to determine if components used in the prosthesis are appropriate to fit the user properly or should be changed to better fit the user in connection with the activities in which the user has been engaging.

12. The method of claim 1, wherein the step of processing the data further includes the step of characterizing the groups of data based on a desired scheme, to represent a plurality of biomechanical events experienced by the prosthesis, in regard to a magnitude of at least one parameter selected from a group of parameters consisting of a force and a moment applied to the prosthesis.

13. The method of claim 12, wherein the step of processing the data further includes the steps of determining:
(a) a location for a center of pressure on a portion of the prosthesis; and
(b) the plurality of moments acting on the prosthesis, based on the force components and the center of pressure.

14. The method of claim 12, wherein the step of processing the data further includes the step of automatically preparing a report for at least one of the user and a medical practitioner, wherein the report presents results from the step of characterizing the groups of data based on the desired scheme, so as to represent the plurality of biomechanical events.

15. The method of claim 1, further comprising the step of using the data with a model to predict at least one of where and when soft tissue breakdown will occur as a result of use of the prosthesis by the user.

16. The method of claim 1, further comprising the step of using the data with a model to assess an alignment of components of the prosthesis and to determine any change that should be made to correct a problem with the alignment.

17. The method of claim 1, further comprising the step of employing results of the step of processing the data to determine if the activities in which the patient engages are cause for changing the prosthesis or a component of the prosthesis used by the patient.

18. The method of claim 1, wherein the one or more pre-loaded piezoelectric sensors are pre-loaded between two plates so as to allow tension and compression measurements along a sensing axis of the piezoelectric sensors, provide more linear performance, and reduce axial force measurement distortions due to sagittal bending moments.

19. The method of claim 18 wherein the one or more pre-loaded piezoelectric sensors are pre-loaded using a bolt which passes through a center of the one or more pre-loaded piezoelectric sensors and couples the two plates together.

20. The method of claim 1, wherein the one or more pre-loaded piezoelectric sensors monitor forces, singly or in combination, in three axes.

21. The method of claim 19, further comprising at least one strain gauge for measuring moments in the transverse plane.

22. The method of claim 1, wherein the data segments are characterized into groups by comparing the difference between the maximum and the minimum of the applied force or moment of the data segment to a predetermined percentage of the applied force or moment measured by the one or more pre-loaded piezoelectric sensors.

23. The method of claim 22, wherein the predetermined percentage of the applied force or moment measured by the one or more pre-loaded piezoelectric sensors comprises 10-15% of the applied force or moment measured by the one or more pre-loaded piezoelectric sensors.

24. The method of claim 22, wherein data segments are characterized into a static group when the difference is less than the predetermined percentage of the applied force or moment measured by the one or more pre-loaded piezoelectric sensors and wherein data segments are characterized into a nonstatic group when the difference is greater than the predetermined percentage of the applied force or moment measured by the one or more pre-loaded piezoelectric sensors.

25. The method of claim 24, wherein the data segments of the static group is further separated into subgroups based on a position of the applied force on a bottom of a foot of the prosthesis.

26. The method of claim 25, wherein the data segments of the static group are separated into a forefoot loading subgroup when the position of the applied force on the bottom of the foot of the prosthesis is anterior to an arch of the foot, a hindfoot loading subgroup when the position of the applied force on the bottom of the foot of the prosthesis is posterior to the arch of the foot, and a balanced loading subgroup when the position of the applied force on the bottom of the foot of the prosthesis is in the arch of the foot.

27. The method of claim 26, wherein the data segments of the forefoot loading subgroup, the hindfoot loading subgroup, and the balanced loading subgroup of the static group are each characterized based on a magnitude of the applied force relative to a weight of the user.

28. The method of claim 27, wherein the data segments of each of the forefoot loading subgroup, the hindfoot loading subgroup, and the balanced loading subgroup are characterized into a low subgroup of each of the forefoot loading subgroup, the hindfoot loading subgroup, and the balanced loading subgroup when the magnitude of the applied force is less than 30% of the weight of the user, a medium subgroup of each of the forefoot loading subgroup, the hindfoot loading subgroup, and the balanced loading subgroup when the magnitude of the applied force is between 30% and 70% of the weight of the user, and a high subgroup of each of the forefoot loading subgroup, the hindfoot loading subgroup, and the balanced loading subgroup when the magnitude of the applied force is greater than 70% of the weight of the user.

29. The method of claim 24, wherein the data segments of the nonstatic group are further separated into a cyclic subgroup and an isolated subgroup based on whether the applied force or moment measurements contain a repeated portion.

30. The method of claim 29, wherein the data segments of the cyclic subgroup and isolated subgroup are further separated into a forefoot loading subgroup of each of the cyclic and isolated subgroups when a position of the applied force on a bottom of a foot of the prosthesis is anterior to an arch of the foot, a hindfoot loading subgroup of each of the cyclic and isolated subgroups when the position of the applied force on the bottom of the foot of the prosthesis is posterior to the arch of the foot, and a balanced loading subgroup of each of the cyclic and isolated subgroups when the position of the applied force on the bottom of the foot of the prosthesis is in the arch of the foot.

31. The method of claim 30, wherein the data segments of the forefoot loading subgroup, the hindfoot loading subgroup, and the balanced loading subgroup of the cyclic and isolated subgroups are each characterized based on a magnitude of the applied force relative to a weight of the user.

32. The method of claim 31, wherein the data segments of each of the forefoot loading subgroup, the hindfoot loading subgroup, and the balanced loading subgroup of the cyclic and isolated subgroups are characterized into a low subgroup of each of the forefoot loading, the hindfoot loading, and the balanced loading subgroups of the cyclic and isolated subgroups when the magnitude of the applied force is less than 30% of the weight of the user, a medium subgroup of each of the forefoot loading, the hindfoot loading, and the balanced loading subgroups of the cyclic and isolated subgroups when the magnitude of the applied force is between 30% and 70% of the weight of the user, and a high subgroup of each of the forefoot loading, the hindfoot loading, and the balanced loading subgroups of the cyclic and isolated subgroups when the magnitude of the applied force is greater than 70% of the weight of the user.

33. The method of claim 29, further comprising:
processing the data segments of at least one of the cyclic and isolated subgroups to identify a stance phase in one or more of the data segments;
extracting the stance phase;
conducting a spectral analysis on the stance phase to identify a perturbation associated with unstable coupling of the prosthesis.

* * * * *